United States Patent
Holm-Kennedy

(10) Patent No.: US 10,072,291 B2
(45) Date of Patent: Sep. 11, 2018

(54) ULTRASENSITIVE BIOSENSORS

(71) Applicant: University of Hawaii, Honolulu, HI (US)

(72) Inventor: James Holm-Kennedy, Honolulu, HI (US)

(73) Assignee: UNIVERSITY OF HAWAII, Honolulu, HI (US)

( * ) Notice: Subject to any disclaimer, the term of this patent is extended or adjusted under 35 U.S.C. 154(b) by 0 days.

(21) Appl. No.: 14/799,364

(22) Filed: Jul. 14, 2015

(65) Prior Publication Data

US 2016/0002707 A1    Jan. 7, 2016

Related U.S. Application Data

(60) Division of application No. 13/733,360, filed on Jan. 3, 2013, now Pat. No. 9,109,251, which is a continuation of application No. 13/535,817, filed on Jun. 28, 2012, now abandoned, which is a continuation of application No. 12/660,534, filed on Mar. 1, 2010, now abandoned, which is a continuation of application No. 11/167,903, filed on Jun. 27, 2005, now Pat. No. 7,692,219.

(60) Provisional application No. 60/582,959, filed on Jun. 25, 2004, provisional application No. 60/582,760, filed on Jun. 25, 2004, provisional application No. 60/582,928, filed on Jun. 25, 2004, provisional application No. 60/582,952, filed on Jun. 25, 2004.

(51) Int. Cl.

| | | |
|---|---|---|
| *C12Q 1/686* | (2018.01) | |
| *B82Y 10/00* | (2011.01) | |
| *B82Y 15/00* | (2011.01) | |
| *H01L 29/06* | (2006.01) | |
| *H01L 29/66* | (2006.01) | |
| *G01N 27/414* | (2006.01) | |
| *H01L 29/49* | (2006.01) | |

(52) U.S. Cl.
CPC .............. *C12Q 1/686* (2013.01); *B82Y 10/00* (2013.01); *B82Y 15/00* (2013.01); *G01N 27/4145* (2013.01); *H01L 29/0665* (2013.01); *H01L 29/0673* (2013.01); *H01L 29/66439* (2013.01); *H01L 29/4908* (2013.01)

(58) Field of Classification Search
CPC ........ H01L 2924/0002; H01L 29/4908; C12Q 2565/607; C12Q 1/6837; C12Q 1/6825; C12Q 2565/515; C12Q 1/02; C12Q 1/66; C12Q 1/6832; C12Q 2565/501; C12Q 2565/518; C12Q 1/003; C12Q 1/005; C12Q 1/58; C12Q 2600/156; G01N 27/414

See application file for complete search history.

(56) References Cited

U.S. PATENT DOCUMENTS

| | | |
|---|---|---|
| 6,111,280 A | 8/2000 | Gardner et al. |
| 6,846,654 B1 | 1/2005 | Blackburn et al. |

(Continued)

*Primary Examiner* — Davienne Monbleau
*Assistant Examiner* — Leslie Pilar Cruz

(57) ABSTRACT

The present invention is a biosensor apparatus that includes a substrate, a source on one side of the substrate, a drain spaced from the source, a conducting channel between the source and the drain, an insulator region, and receptors on a gate region for receiving target material. The receptors are contacted for changing current flow between the source and the drain. The source and the drain are relatively wide compared to length between the source and the drain through the conducting channel.

18 Claims, 17 Drawing Sheets

(56) References Cited

U.S. PATENT DOCUMENTS

| | | |
|---|---|---|
| 6,872,298 B2 | 3/2005 | Kermani |
| 7,888,013 B2 | 2/2011 | Miyahara et al. |
| 2004/0007740 A1 | 1/2004 | Abstreiter et al. |
| 2004/0134798 A1* | 7/2004 | Toumazou ........... C12Q 1/6825 205/793.5 |
| 2005/0116263 A1 | 6/2005 | Lu et al. |
| 2005/0136423 A1* | 6/2005 | Paulus ............... G01N 33/5438 435/6.1 |

* cited by examiner

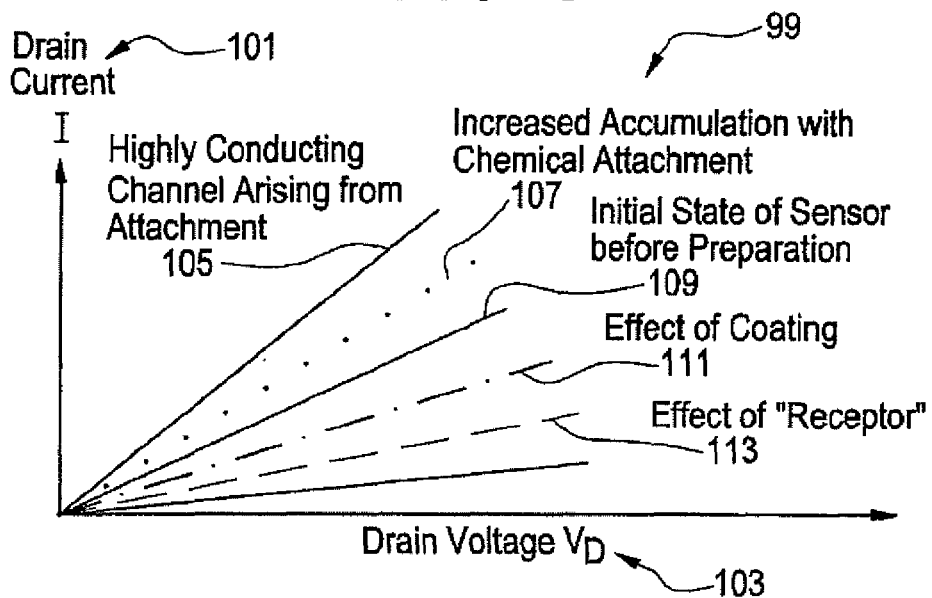
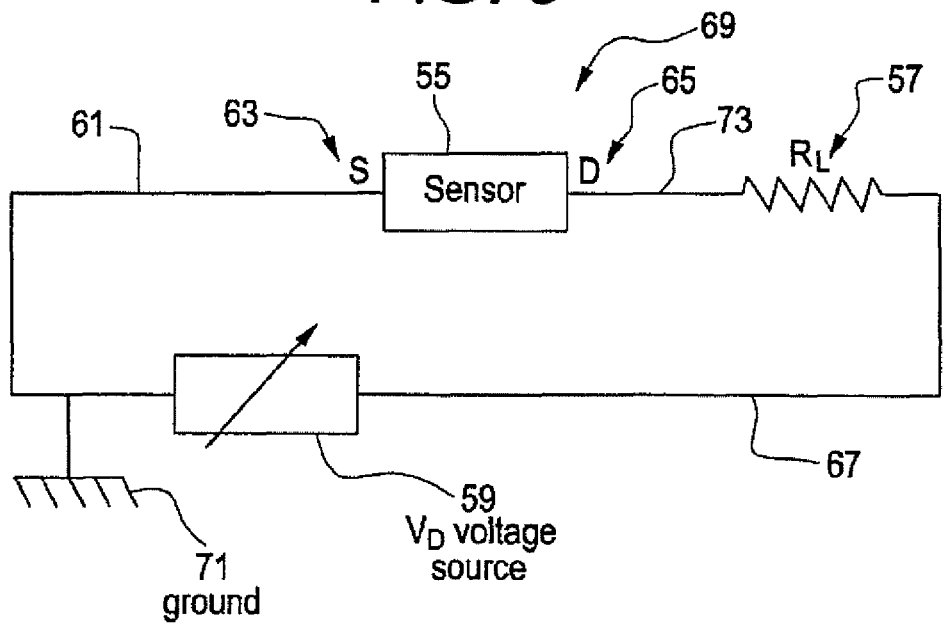

ULTRASENSITIVE BIOSENSORS

CROSS-REFERENCE TO RELATED APPLICATIONS

This application is a divisional of U.S. application Ser. No. 13/733,360 filed Jan. 3, 2013, which is a continuation of U.S. application Ser. No. 13/535,817 filed Jun. 28, 2012, which is a continuation of U.S. application Ser. No. 12/660,534 filed Mar. 1, 2010 (now abandoned), which is a continuation of U.S. application Ser. No. 11/167,903 filed Jun. 27, 2005 (now U.S. Pat. No. 7,692,219), and claims priority to U.S. application No. 60/582,760 filed Jun. 25, 2004, U.S. application No. 60/582,952 filed Jun. 25, 2004, U.S. application No. 60/582,928 filed Jun. 25, 2004, and U.S. application No. 60/582,959 filed Jun. 25, 2004, which disclosures are herein incorporated by reference in their entirety.

BACKGROUND OF THE INVENTION

Biosensors have been and are being developed to detect, identify and quantify various biochemicals, ranging from proteins to toxins to RNA to c-DNA to oligos and to disease agents such as viruses, bacteria, spores and Prions. This list is by way of example, and is not intended to be complete. Some biosensors sense charge on the molecule. Many biochemicals carry a net charge. Electrophoresis methods and various blots exploit molecule net charge to affect physical separation of such molecules.

There is a significant problem with existing techniques such as electrophoresis and the various blots. These sensors are not specific in identifying the molecules in question unless significant post processing and labeling is employed. Further, a very large quantity of the tested biochemical is required for electrophoresis detection methodologies.

In many instances the number of molecules available for detection is very small and may be below the sensitivity threshold of the sensor, or may be problematic with respect to sensitivity. For example, some plasma proteins are of very low concentration. Toxins such as Botulinum toxin are notoriously hard to detect at lethal thresholds because of their very low lethal and sub-lethal, but still dangerous, concentrations. Mass spectroscopy requires a large number of molecules in order to achieve adequate detection sensitivity.

In the case of c-DNA and RNA sensing, the number of base pairs or nucleotides present may be low creating a problem for adequate detection and identification. This is possible if, for example, only a few bacteria are present or the RNA is of low concentration because of either the desired identifying component or small virus count. Virus RNA may be of low density for samples monitoring air. Only a small portion of the RNA may provide the definitive identification signature. Overall these sensing environmental aspects may lead to a relatively small amount of RNA or DNA actually involved in the definitive detection process.

In the case of proteins, the target molecule concentration may be very low in the sample. For example, with Prions (mad cow disease), if a fluid sample is taken from an animal's blood, the target protein concentration can be very low compared to that taken from brain tissue. With early infection of humans, animals or plants with disease, the initial signature indicators may be present in only very small concentrations. Signature bio compounds for a liver infection at its onset or signature proteins in the very early stages of cancer, when one wishes to identify disease presence, are typically of very low concentration. Key definitive disease indicators may be present in only very small concentrations.

Where only small concentrations of target molecules are available, mass action effects can result in the bound target concentration being very low. A small percentage of the actual receptors, e.g., specific antibodies to the target molecule, available for bonding of the target molecules can result in a very small detection signal. For example, consider the case of a lethal concentration of botulinum toxin. Only a very tiny fraction of the receptors (recognition elements) are bound, perhaps 1 in 3000 antibodies. At the very earliest onset of disease, the density of indicative proteins, viruses, antibodies and bacteria may be very low, thus placing a very high sensitivity measurement burden on the sensing approach.

Sensors for the detection of target molecules using charge have been reported. The most commonly used to date are those using electrophoreses methods, such as the various blots. Semiconductor charge sensors have long been highly sought after due to their compatibility with integrated circuits and attendant low cost batch manufacturing processes. An example is the ImmunoFET that uses a conventional MOSFET, absent a metal gate, and employing a reference electrode in solution. This approach is problematic resulting in drift and small signals.

Biochemicals such as proteins and receptors often carrier charge. By way of example, blots and electrophoresis exhibit details of such biochemical incorporated net charge. The amount of charge on the biochemical is often pH dependent.

When measuring attached charge arising from biochemicals bound to a biosensor, the link to the density of molecules attached incorporates knowledge of how much charge is bound by each molecule. Such bound bimolecular charge is well known to depend on pH.

Some measurements are usefully performed at different or variable pH values. Indeed, the charge dependence on pH can provide some confirmation that the biomolecule attaching is the one expected or targeted.

Semiconductor devices are often temperature dependent. While temperature-correcting circuits may be integrated and invoked to correct the measurement output for temperature influences, an alternative method is to measure the temperature and correct the sensor output, e.g., using a look up table.

Temperature can be used to affect molecular dissociation as is commonly done with DNA. The temperature at which such dissociation occurs is a measure of nucleotide binding and molecule details. Temperature measurement under these conditions can provide useful quantitative information related to the biochemical.

While external means may be employed to change the sample environment's temperature, it is more convenient at times to control the temperature change on chip automatically. This is done using a heater feedback systems linked to a temperature monitor.

PCR incorporates thermal cycling. Incorporation of PCR with selective sensors can provide utility. For example, the thermal cycling may be combined with suitable wash steps and reinsertion into the reaction region to collect target molecules provides a means for collection of targeted molecules. By way of example, such target molecules may be RNA molecules or antibodies. Other examples are possible.

There is a need in medical science for reliable, low costs medical diagnostics, as well as reliable and robust universal biochemical sensors for disease diagnostics.

Needs exist for biochemical sensors that provide an electrical output sensing parameter that is easily measured.

The biosensors need to be suitable for automated testing, e.g. to be employed in medical laboratories that manage large numbers of diagnostics samples. Biochemical sensors must be able to interrogate a sample for any one of many targets or diseases simultaneously.

Improved biosensors need to be compatible with electronics in general and with integrated circuit technology in particular. Such biosensors would easily access a wealth of known integrated circuit (IC) technologies and integrated circuit electronic means of measurement and interrogation.

There is a need for biochemical sensors with high sensitivity (for low target concentrations and multiple target diagnostics) and which can be easily measured to provide details of biochemical detection details.

Ease of measurement is an important desirable biosensor feature. Ideally a simple multimeter and, if needed, a simple power supply are used. To address these, the sensor designs must be such as to provide ease of measurement.

There is a need for low cost biosensors. Batch processing technology offers advanced low cost manufacturing processes for fabrication of many types of electronic devices and circuits. IC batch processing can be used to manufacture very low cost biosensors. IC technologies are particularly attractive since these are readily available in IC foundries. Such technologies include, but are not limited to, polysilicon deposition, doping (including ion implantation), surface state control processes, patterning and photolithography. In the best manufacturing case, such technologies best do not push to nanometer dimensions due to costs, low yields and other adverse features. It is desirable to ensure consistent device performance and sensor arrays (hybrid or integrated on chip) with all or the vast majority of sensors working, all compatible with convenient measurement range using readily available instrumentation or circuit design. Excessive need for signal processing adds costs.

Needs exist for biosensors that are not prone to 60, 120 Hertz, microphonics or other interfering pickup from stay interfering signals in the environment.

There is a need for sensor arrays that can be used to simultaneously tests for multiple targets in an environment. Such arrays should be incorporate sensing components that are easily measured using conventional circuitry and/or instrumentation and not push signal processing limitations.

Biosensor arrays with sensor spacing compatible with robotic liquid handling (spotting) are needed to provide multiple target recognition element placement without bleeding of spots. Bleeding of spots can undesirably corrupt specific recognition objectives of adjacent sensors in the array.

There is a need for automated circuit support of biochemical sensor arrays. Semiconductor technologies, especially silicon IC technologies, can provide integrated circuit needed function in circuit form on the same chip as one or more sensors.

Needs exist for sensors and sensor arrays compatible with simple packaging schemes.

Sensors should be compatible with both advanced IC technologies and advanced biochemical technologies. Biochemical technologies can be integrated with Si technology to incorporate a wide range of recognition element suitable for targets such as those listed in Table 7.

There is a need for biosensors that are insensitive to moisture and fluids found in the testing environments. Typically, semiconductor based devices show a significant moisture sensitivity leading to erroneous measurements. Sensing for targets in a liquid such as water or blood plasma is a requisite for biochemical sensors. Water, plasma or other target containing liquids should not significantly influence the sensor. The same is true for the attachment of recognition elements incorporating a liquid carrier. Whereas there are methods to provide water protection for Si integrated circuits, these methods necessarily often introduce undesirable features that are undesirable, for example, emersion in a binding epoxy resin. In particular, very thin insulating over layers are suitable for measuring contact potential of a coating or partial coating material. However, such thin over layers typically do not well protect against water contamination.

There is a need to provide overlaying insulators which are thin to ensure excessive stress is not developed, such as can occur for very thick $Si_3N_4$ layers.

Needs exist for sensitive biosensors that have low cost measurement instrumentation requirements. To be widely employed, the attendant biosensor instrumentation needs to be low cost.

There is a need to provide sensitive biosensors which use measurement instrumentation for which health workers can easily be trained, and/or which equivalent instrumentation can be provided on chip in support of simple diagnostic readout devices.

Biosensors are needed for being employed successfully, without loss of utility, where inhomogeneous target or recognition element attachment has occurred. That is, inhomogeneous influences on the sensor conducting regions caused by inhomogeneous recognition element and/or target attachment should not be problem in introducing errors in either detection or quantification.

There is a need for biosensors that use relatively simple circuitry to provide an instrumentation or measurement function, on chip.

Easy remote sensing of biosensors is needed. Such addresses needs for homeland defense. Remote sensing further supports disease diagnostics, for example in remote regions where unskilled workers may be attending the ill, which may, by way of example, be important in tracking the spread of an epidemic or pandemic.

There is a need for biosensors that enable hybrid or integrated sensor arrays that are easily integrated into communications and automated measurement systems.

Needs exist for semiconductor biosensors that are compatible with standard integrated circuit technologies, such as CMOS technology.

Improved pathogen detection sensitivity, which can be affected using compound semiconductor high mobility materials, is needed.

There is a need for very high sensitivity biosensors that can detect multiple present diseases with a single low cost device.

Needs exist for high sensitivity simple biosensors that can incorporate only a few expensive recognition elements where said recognition elements are very expensive. The more sensitive the device, generally the fewer recognition elements are needed. Larger dimension devices are design for sensitivity and can detect many different targets and keep the recognition element costs low. For example, reducing the number of antibodies needed for detection by a factor of 100 reduces antibody costs by a factor of 100. Spread over millions of biosensors, this cost saving is substantial.

There is a need for chemical sensors that can provide a measurement of the Gibbs free energy of a material, i.e., measure the Fermi level of the material. For example, such devices can be used to monitor environmental degradation of materials.

Avoiding unwanted surface trapping states is desirable when it would diminish or eliminate the electric field influences on the conducting channel free carriers. There is a need to avoid charge screening of the target charge.

Needs exist to provide a large enough signal such that the influence of the target attachment is easily measured with relative simple instrumentation or circuits, such as an ohmmeter. This need relates to resolution of multiple binding of targets and the ability to make reliable measurements at low cost.

Sufficiently large area devices are needed if robotic spotters are to be used to apply recognition elements at different locations, either on the same bioresistor or on arrays of bioresistors. If the bioresistor's surface is sufficiently large, high sensitivity designs permit multiple target sensing on a single sensors. There is a need for sensors to be of sufficient dimension such that robotic spotters can apply local attachment of pre-selected recognition elements. While such robotic systems can apply multiple chemical mixes to different location on a single chip, the minimum size of the liquid spot is limited. Bleeding from one sensor to an adjacent sensor can occur if the sensors are sufficiently small and densely arrayed. Such cross mixing is adverse and can introduce errors of measurement and false positives or false negatives. For example, substantially sub micron or nano dimensional electrical sensors are generally undesirable for these and other reasons.

There is a need for the biosensor active area to be sufficiently large to define pH controlling mixed functional groups in order to help ensure a constant pH at the sensor surface and avoid unwanted and unknown localized pH fluctuations which may affect the charge on the target, as is known to be a function of pH.

Needs exist for highly sensitive biosensors that can sense very low concentrations.

SUMMARY OF THE INVENTION

The present invention is a biosensor apparatus that includes a substrate, a source on one side of the substrate, a drain spaced from the source, a conducting channel between the source and the drain, an insulator region, and receptors on a gate region for receiving target material. The receptors are contacted for changing current flow between the source and the drain. The source and the drain are relatively wide compared to length between the source and the drain through the conducting channel to address sensor electrical output characteristic requirements.

The insulator region and the gate region are relatively wide compared to their length and to the length between the source and the drain. The source, the drain, the conducting channel, the insulator region and the gate region are a field effect transistor for controlling current between the source and the drain in response to applied voltage and to the target materials in contact with the receptors on the gate region.

Preferably, a circuit is connected between the drain and the source, a voltage potential connected to the circuit and an multimeter connected to the circuit for measuring current in the circuit and resistance between the source and the drain and determining changes in resistance for calculating influence of the target material on the gate region. The sensor comprises a first sensor and wherein the substrate, the source, the drain, the conducting channel, the insulator region and the gate region comprise a first substrate, a first source, a first drain, a first conduction channel, a first insulator region and a first gate region, and further comprises a second sensor a second substrate, a second source, a second drain, a second conduction channel, a second insulator region and a second gate region, and wherein the first and second insulator regions are respectively relatively thin and relatively thick for separating attached charge and chemical potential changes when determining changes in resistance.

The sensor may include a first sensor and wherein the substrate, the source, the drain, the conducting channel, the insulator region and the gate region comprise a first substrate, a first source, a first drain, a first conduction channel, a first insulator region and a first gate region, and further comprises a second substrate, a second source, a second drain, a second conduction channel, a second insulator region and a second gate region.

The apparatus also may include a circuit. The output of the circuit provides a parameter for providing a measurement of sensor response to target binding. The parameter is resistance, voltage, current, time delay, frequency, charge, amplification of current or voltage, frequency mixing including sum and different frequencies, capacitance, or a combination of these parameters.

The conducting channel may be doped for providing positive mobile charge holes or negatively conducting electrons in the doped channel and providing reverse bias control of the gate region depletion via the PN isolating junction. Positive mobile charge conducting holes in the conducting region may be increased upon negatively charged target material attaching to the receptors. Forming the source and the drain as spaced meander lines in or on the substrate provides the relative width compared to length.

In an alternative embodiment a biosensor apparatus includes a substrate, a source on one side of the substrate, a drain spaced from the source, a conducting channel between the source and the drain, an insulator region, and receptors on a gate region for receiving target material. The receptors are contacted for changing current flow between the source and the drain. The conducting channel and the insulator region and the gate region have relatively long length between the source and the drain compared to width of the source, the drain, the conducting channel, the insulator region and the gate region.

The target materials may be biological materials.

The present invention is also a method of sensing target materials including providing a substrate, providing a source in or on the substrate, providing a drain in or on the substrate spaced from the source, providing a conducting channel in or on the substrate between the source and the conducting channel, providing an insulator region on the conducting channel and on the substrate, providing a gate region on the insulator region, and providing receptors on the gate region and controlling relative widths and lengths of the source, the drain, the conducting channel, the insulator region and the gate region and thereby controlling sensitivity to the target materials.

The method may also include providing relatively large widths of the source, the drain, the conducting channel, the insulator region and the gate region with respect to lengths of the source, the drain, the conducting channel, the insulator region and the gate region between the source and the drain for increasing sensitivity to the target materials.

The method may also include providing relatively large lengths of the source, the drain, the conducting channel, the insulator region and the gate region with respect to widths of the source, the drain, the conducting channel, the insulator region and the gate region between the source and the drain for increasing sensitivity to the target materials in saturation ranges of the sensing.

The providing of the source, the drain, the conducting channel, the insulator region and the gate region includes providing a first source, a first drain, a first conducting channel, a first insulator region and a first gate region, and further comprising providing a second source, a second drain, a second conducting channel, a second insulator region and a second gate region, and providing the first insulator region relatively thin and the second insulator region relatively thick for sensing changes in resistance and concurrently sensing changes resistance in on the first and second gate regions.

The method also includes providing a circuit. The output of the circuit provides a parameter for providing a measurement of sensor response to target binding. The parameter is resistance, voltage, current, time delay, frequency, charge, amplification of current or voltage, frequency mixing including sum and different frequencies, capacitance, or a combination of these parameters.

The method also includes providing a load resistance in the circuit and measuring potential drop across the load resistance.

Another embodiment of a sensor apparatus includes a substrate, an epitaxial layer disposed on the substrate, a first ohmic contact on the substrate, a second ohmic contact on the substrate spaced from the first ohmic contact, a conducting mesa etched in the epitaxial layer between the first and second ohmic contacts, a functionalized surface overlying the epitaxial layer, a biochemical receptor region on the functionalized surface, and conducting interconnections connected to the first and second contacts.

The conducting interconnections may extend through the epitaxial layer. A PN junction may be formed between the epitaxial layer and the substrate. This embodiment may also include a depletion region in the substrate under the conducting mesa, and a back gate biasing circuit connected to the substrate.

The epitaxial layer may be doped with a different P or N type from the substrate. The epitaxial layer may be a first epitaxial layer and further include a second epitaxial layer positioned on the substrate between the substrate and the first epitaxial layer.

The conducting mesa etched epitaxial layer may be a polysilicon N or P type resistor. Insulators may be positioned on the polysilicon resistor. The functionalized surface may be a resistor protective layer and the receptors may be recognition elements attached to the resistor protective layer. Multiple distinct recognition elements may be attached to the resistor protective layer for testing distinct target materials. The resistor may be constructed with specific etched mesa constructions near the distinct recognition elements. The resistor may be a meanderline resistor.

There may be an array of sensors polysilicon N or P type resistors. An array may include addressing circuitry connecting the array of sensors, and an array output.

The sensor apparatus may also include temperature sensor and a pH sensor on the substrate. A feedback system for temperature control and a heater resistor may be included.

These and further and other objects and features of the invention are apparent in the disclosure, which includes the above and ongoing written specification, with the drawings.

BRIEF DESCRIPTION OF THE DRAWINGS

FIG. 3 shows I-V characteristics for the sensor configuration in FIGS. 1A-1C.
FIG. 5 shows a simple voltage divider system.

DETAILED DESCRIPTION OF THE PREFERRED EMBODIMENTS

A variety of issues are pertinent to making biosensor measurements relating to the attachment of biochemicals and materials. By way of example, such issues include: sensitivity, ease of measurement by non-engineers, instrumentation availability and convenience, and ease of converting measurement information to biochemical attachment, charge and chemical potential information.

Advantages for circuit and instrumentation use and function, by way of example, include: measurement sensitivity, ease of linking measured data to biochemical quantitative information, ease of measurement, speed, sensor array measurement management, support of automated measurement, support of remote sensing, support of radio linked test reporting, and instrumentation cost.

Various instrumentation options may be integrated with the biosensors. By way of example, three approaches are provided for illustrative examples that employ specific design approaches. The uses require particular device configurations and are provided by way of example.

Instrumentation examples include measurement of resistance, RC oscillator inputs, and load line voltage division.

Figure 1B:
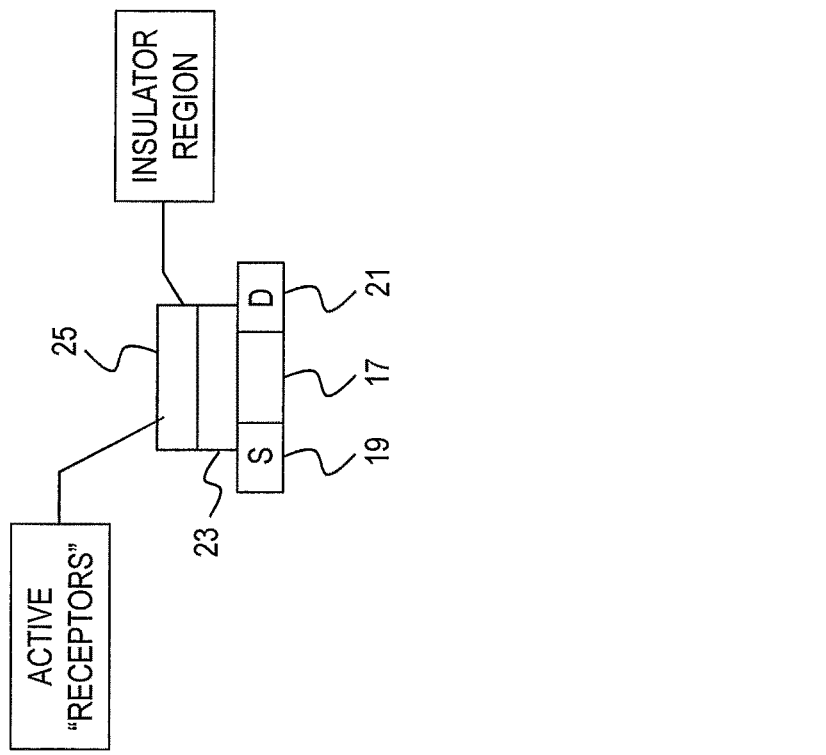
FIGS. 1A and 1B are schematics of a large W/L biosensor.
Figure 1A:
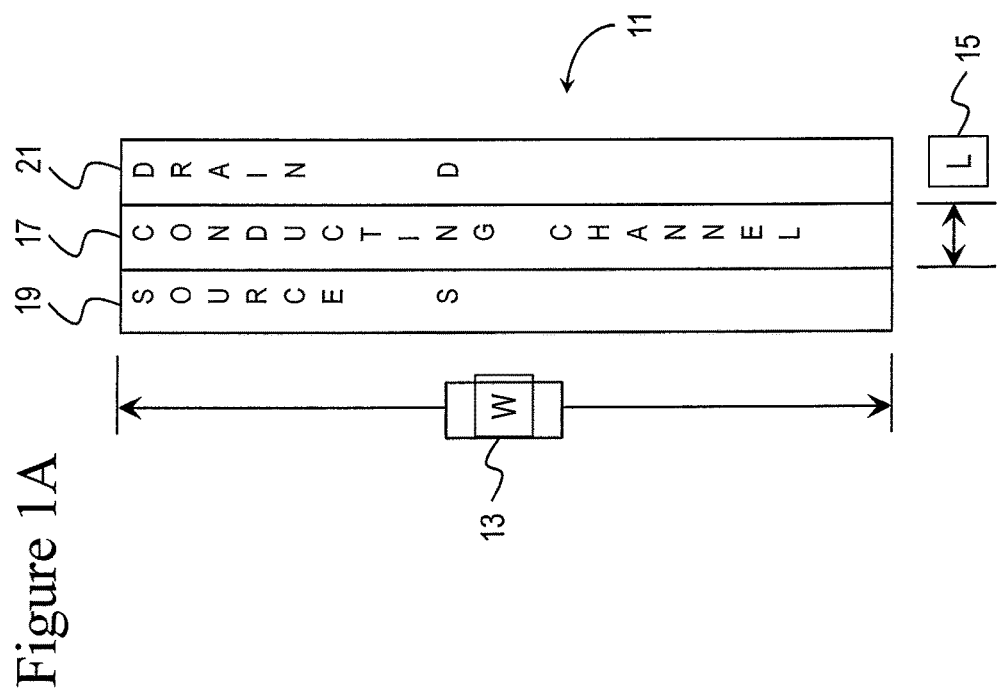
Figure 1C:
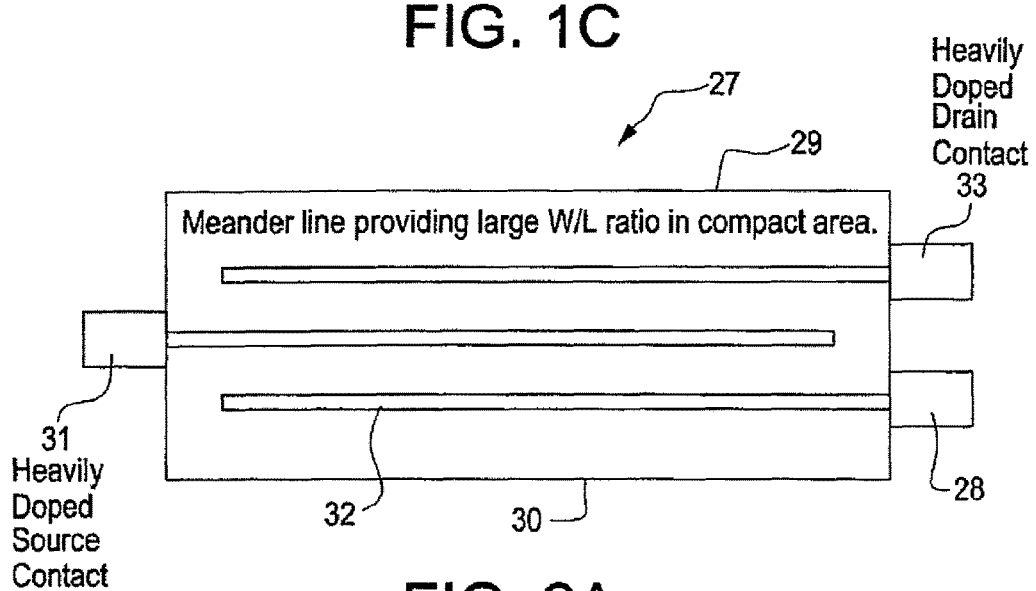
FIG. 1C is a large W/L ratio biosensor in a meander line format.

Measurement of Resistance. The electrical characteristics indicated in FIG. 3 show a linear relationship between drain voltage and drain current for a large collection of biochemical measurement target parameters. The linearity means a single resistance describes the sensor condition and the related influencing materials. By using a simple ohmmeter or voltmeter, the condition of the sensor is measured. By comparing the resistance of one measurement with the previous measurement, the direct influence of the biochemical change (such as the attachment of a target molecule) arising from biochemical or material attachment is calculated. A relatively simple computation is used to translate the change in resistance to a change in gate attached charge or chemical potential. Two devices of differing insulator thickness may be used to separate attached charge and chemical potential changes if both are present and influencing the measurements. This sensor configuration is illustrated in FIGS. 1A-1C. The related I-V electrical characteristics are schematically represented in FIG. 3.

FIGS. 1A and 1B show a large W/L biosensor 11. The ratio of the width 13 over the length 15 scales the resistance of a channel 17. A source 19 and a drain 21 are located on opposite sides of the channel 17. An insulator region 23 is located over the channel 17. A gate region 25 with receptors is located over the insulator region 23. All other design parameters being equal (channel doping, etc.), the large W/L ratio corresponds to a larger resistance for the same channel conductivity (e.g., channel doping or channel inversion or channel enhancement). Here the saturation region is not accessed until much higher voltages due to the channel short length L. The narrow channel width ensures high current flows (low resistance) relative to a wider channel before saturation sets in. The long length L ensures high current flows at very low drain voltages and light channel carrier concentrations.

FIG. 1C is a large W/L ratio biosensor 27 in a meander line format. The large W/L ratio is achieved in a compact manner by forming a meander line 29. A heavily doped source contact 31 is located opposite a heavily doped drain contact 33. Other features, including a biosensing gate and protective insulators, are as formed for other configurations. A substrate back gate bias contact 28 is connected to a substrate back gate 30 underneath a substrate back gate 32.

FIG. 3 shows I-V characteristics for the sensor configuration in FIGS. 1A-1C. The linear characteristics represent a resistance with different resistor values for each test. The resistance is measured using a circuit or even a simple ohmmeter. The order of the curves and their conductances are arbitrarily selected to indicate both chemical potential effects and influences of chemicals containing ions of positive or negative charge. The influence of ions from the buffering or other solutions is indicated only by way of example. The graph 99 measures drain current 101 versus drain voltage $V_D$ 103. Lines indicate various effects including: a highly conductive channel arising from attachment 105, increased accumulation with chemical attachment 107, initial states of sensor before preparation 109, effect of coating 111, and effect of receptors 113. Details vary with the testing system and sensor materials details.

RC Oscillator. A circuit employing a resistance capacitance (RC) combination with a suitable operation feedback amplifier configuration is made to produce a frequency output that is a direct function of the value of R, that is, a direct function of the electrical characteristics as illustrated in FIG. 3. Different sensor conditions relating to different resistances produce different frequency outputs that can be quantitatively converted to biochemical density and specific materials properties, such as chemical potential.

Other oscillators using these general electrical characteristics in FIG. 3 are also possible.

Load line voltage division. A third convenient configuration for measurement of the sensor electrical condition and thus the details of what has attached or not attached to the sensor and what is influencing the sensor output is represented by the load line feature in FIG. 4. This is a well-known load line configuration for FET devices.

Figure 2A:
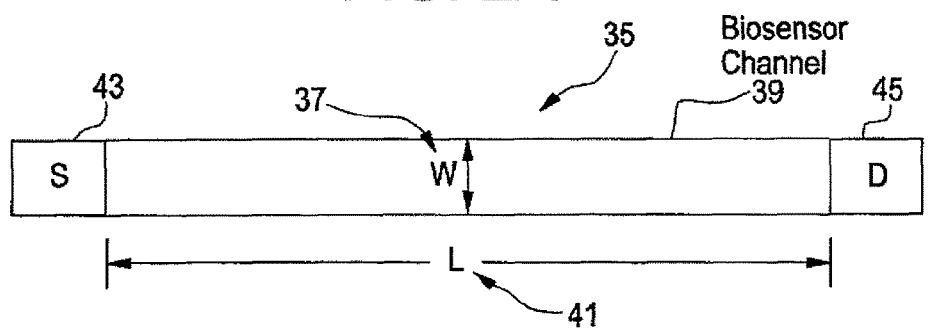
FIG. 2A shows a biochemical sensor with a small W/L ratio.
Figure 2B:
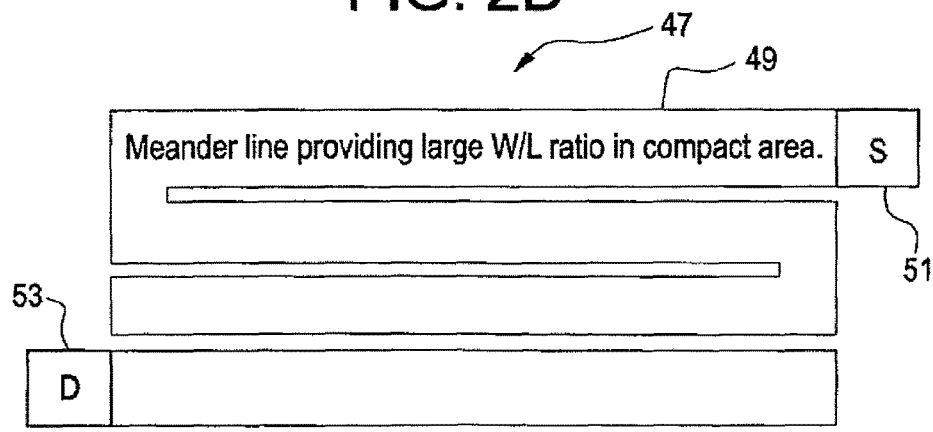
FIG. 2B shows a small W/L channel biosensor using a meander line.
Figure 4:
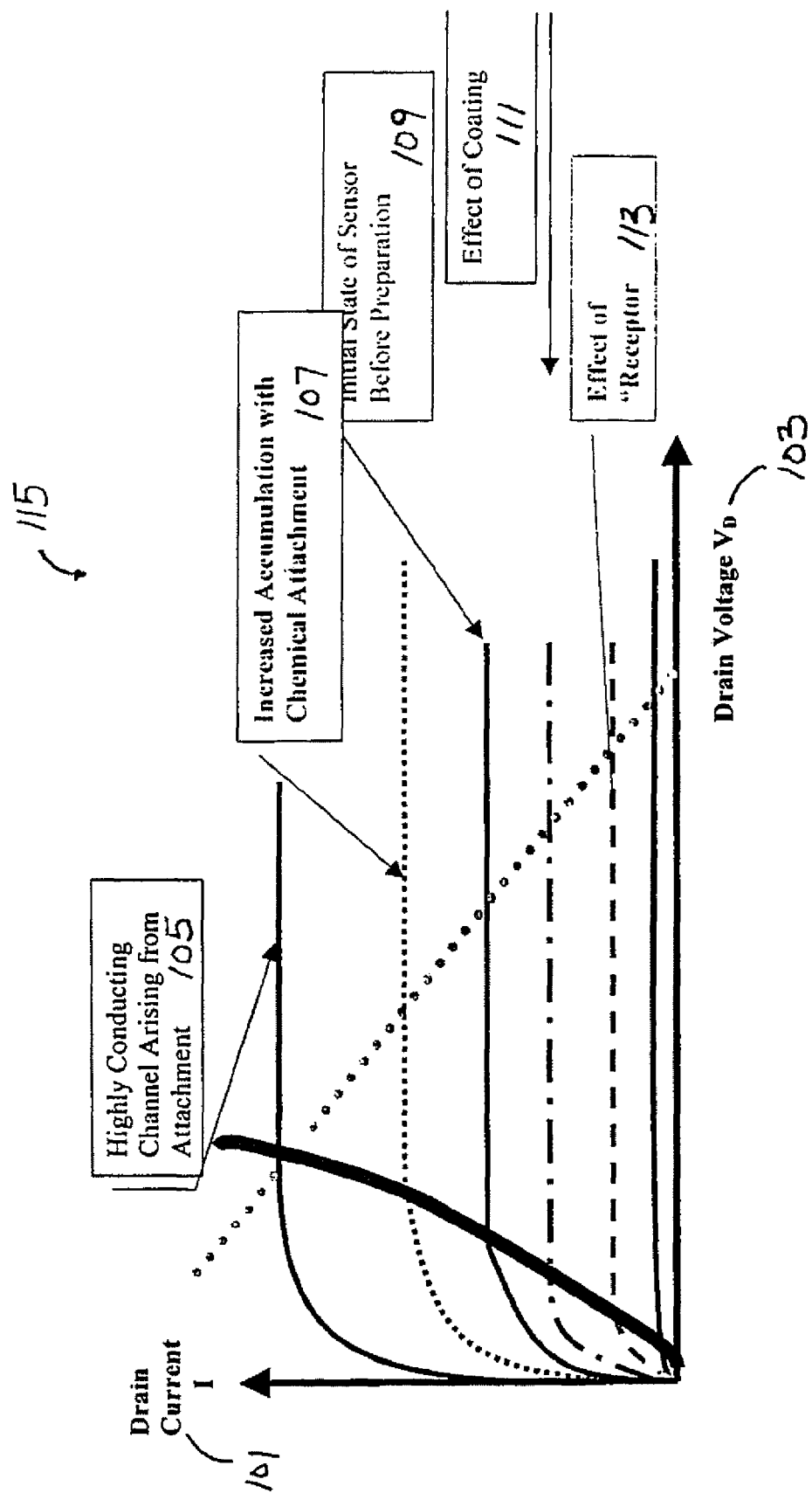
FIG. 4 shows I-V characteristics for the device of FIGS. 2A and 2B.

FIG. 4 shows I-V characteristics for the device of FIGS. 2A and 2B. Here the sensor reaches saturation at modest drain voltages. The linear (resistor) region occurs only at relatively low drain voltages if the channel is lightly doped. The device, when measured properly, displays more sensitivity in the saturation region than in the linear resistor region. The saturation region is to the right of the thick solid line. The graph 115 measures drain current 101 versus drain voltage $V_D$ 103. Lines indicate various effects including: a highly conductive channel arising from attachment 105, increased accumulation with chemical attachment 107, initial states of sensor before preparation 109, effect of coating 111, and effect of receptors 113.

FIG. 5 shows a series configuration of the sensor 55 with a load resistor $R_L$ 57 corresponding to the load line in FIG. 4. FIG. 5 illustrates the circuit. A voltage source 59 is connected 61 on a source side 63 of the sensor 55. Current exits on a drain side 65 of the sensor 55 and is connected 73 to the load resistor 57. Current then is connected 67 back to the voltage source 59 to complete the circuit 69. The circuit 69 may include a ground 71. As the sensor current characteristic changes with sensor conditions (e.g., biochemical attachment), the voltage across the sensor changes.

FIG. 5 shows a simple voltage divider system 69. The drain current may be set to a pre-selected value that ensures the load line traverses the saturation region as illustrated in FIG. 4. As the conductive state changes under the influence of some change in the detection by the biosensor, the intersection of the load line with the electrical characteristic changes, as shown in FIG. 4. One may measure a corresponding shift in the voltage across the load resistor or the compliment across the sensor.

The change in the voltage drop across the load resistor $R_L$ is the exact opposite in sign and equal in magnitude to that change in the voltage across the sensor. Such voltage change is maximized by resistor selection and sensor design. The load line may be selected for a particular sensor to provide the maximum measure sensitivity. For example, a flatter load line (higher resistance) causes a larger voltage change across the resistor (or sensor) with an electrical characteristic shift arising form the sensor response to an external stimulus.

It is emphasized that the sensor may be designed to provide the maximum measurement sensitivity for this configuration.

The following are innovation configurations, sensor basic configurations, sensitivity and measurement relationships.

Large width to length (W/L) ratio. FIG. 1 shows a large W/L design for a biosensor. The short and wide channel provides a relatively large channel conductance. By controlling the W/L value, the channel conductance is adjusted, which is a very important consideration especially for very low attached biosensor signal conditions. For the configuration represented in FIG. 1, a channel doping and back gate bias control of the underlying depletion region are provided to ensure that the device is operating in the linear region in support of measurement methods described in the instrumentation examples.

Figure 6A:
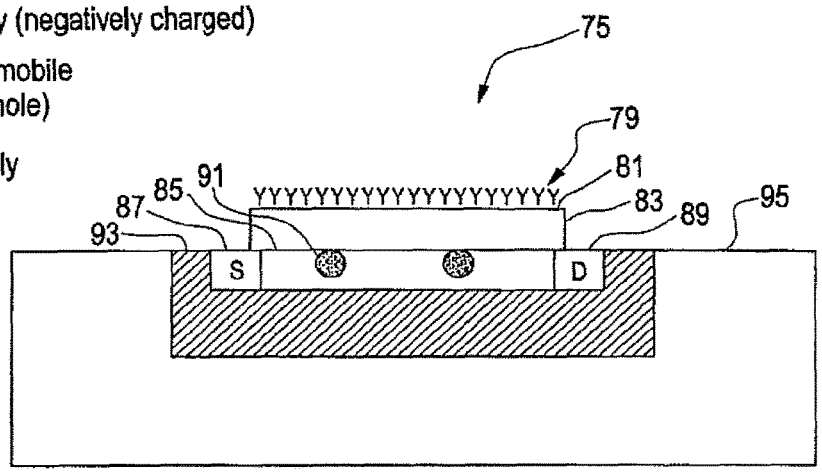
FIG. 6A shows a biosensor under weak channel conduction.

The large value of W/L is particularly important in supporting accurate, high resolution measurements when the channel conductance is very low as is the case when measuring very weak signals originating from low bound target concentrations. FIG. 6A schematically represents the conduction condition created in order to provide ultra sensitivity. This condition is achieved by adjusting the back gate bias and channel doping to force a low channel free carrier concentration, in this case a low hole concentration.

FIG. 6A shows a biosensor 75 under weak channel conduction. Antibodies 79, negatively charged in this example, are attached to a gate region 81 on top of an insulator region 83. The insulator region 83 is attached on a conductance channel 85 between a source 87 and a drain 89. Positive mobile charges 91 are found in the channel 85. An isolation region 93 separated the sensor 75 from a substrate 95. The channel conduction for this device is intentionally made very weak by both channel doping and reverse bias control of the back gate depletion. Here the channel resistance would be too high unless a large W/L configuration is used. W/L here is used to ensure that there is adequate conductance prior to very low concentration of binding target molecules, as shown in FIG. 6B.

Figure 6B:
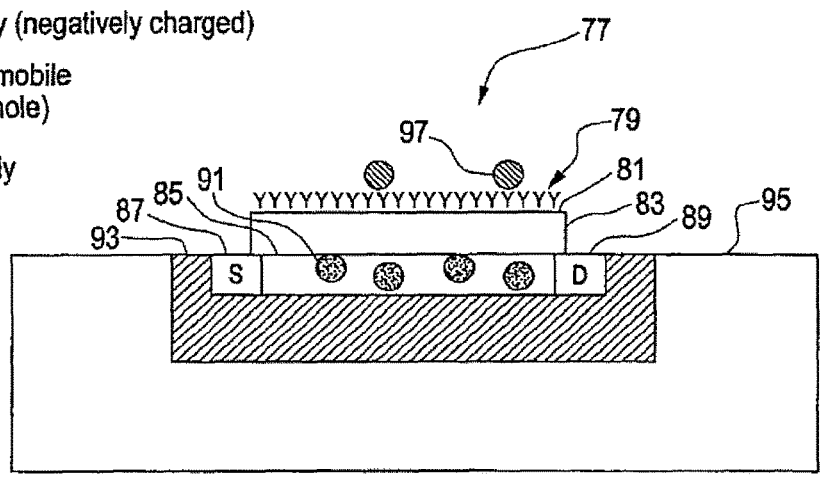
FIG. 6B shows biosensor channel conduction with low concentration target binding.

FIG. 6B shows biosensor 77 channel conduction with low concentration target binding. In this example, negatively charged antigens 97 are attached to the antibodies 79. The channel hole concentration is shown under conditions of very weak attached target concentration. In this example, the concentration of conducting holes has doubled from a very low concentration before target attachment to a still very low concentration, but double that of the initial state shown in FIG. 6A.

When the target molecules are top gate attached in weak concentrations, as indicated in FIG. 6B, the channel resistance decreases (channel conductance increases) in this example of a depleted hole channel (p-channel) with negatively charged target molecules attaching. In this specific schematic example, shown in FIGS. 6A and 6B, the channel resistance has halved and the conductance doubled. Such a change is easy to measure if the channel conductance is still adequate. For such low channel free carriers (holes in this example), the channel conductance is so low that sensor design must be invoked to raise the channel conductance to measurable values. This is done by using a very high W/L channel as illustrated in FIGS. 1A-1C. Here the meander line channel is typically more desirable in order to provide compactness with a very high W/L value.

While ultra sensitivity has been illustrated using a P-channel device for negatively charged target molecules, an N channel device could alternatively be used and the devices may be used for either positively charged or negatively charged molecules.

For ultra sensitive biosensor applications, the device may be measured in the linear region or the saturation region, as shown in FIGS. 3 and 4. The saturation region provides higher trans conductance sensitivity. The linear region provides a convenient "ohmmeter averaging" of the linear signals and can be measured to approximately 5-6 significant figures with commercially available ohmmeters.

The following is a channel design for ultra sensitivity and maximum target detection sensitivity.

One key design parameter is:

$d(\ln(R_{ch})/dV_g$ or $d(\ln(G_{ch})/dV_g$ for linear operation. Here $R_{ch}$ is the channel resistance in the linear region, $dV_g$ is the effective top gate voltage change and $G_{ch}$ is the channel conductance in the linear region. The attached charged molecules result in a pseudo gate voltage on the top gate. Multiplying this $<V_g$ (biochemicals) times the above equation provides a $<R/R$, which is what one wishes to maximize. Similar considerations apply to the saturation region.

Such a high sensitivity condition is illustrated in FIGS. 6A and 6B. The conducting channel has very few charge carriers to carry current. A small attached target concentration, shown in FIG. 6B, in this case doubles the conducting carrier concentration, thereby doubling the conductance or increasing the drain current (linear and saturation regions). The overall value of the resistance or trans conductance is maintained for measurement purposes by using a large W/L value.

For high detection sensitivity producing small signals arising from low attached molecule concentrations, it is important to ensure a low channel free carrier concentration, one that is substantially changed by the attaching targets influence on the channel conductance channel free carrier concentration. The channel conductance is controlled by channel doping and by back gate bias. The overall values of resistance and trans conductance are controlled by W/L values.

Accumulation versus depletion channel devices. It is noted that, in general, to avoid inversion lockup of the channel conductance under high target molecule concentrations and high receptor concentrations, the preferred embodiments are conducting channels that are enhanced by the attaching biochemicals, unless a switching device is intended. The back gate then is used to control the actual concentration of carriers in the conducting channel. Here the term "receptor" is used in the most general sense. A receptor is a chemical that has an affinity for another chemical (target chemical) and generally that affinity is selective and specific to the target chemical. Antibodies are one example, nerve receptors another, drug receptors another, oligos another, and so on.

Low W/L sensors. By designing in a low value of W/L, as shown in FIGS. 2A and 2B, one can force the saturation condition to occur at very low drain voltages ($V_D$). Depending on the details of the magnitude of the sensed targets signal, and the instrumentation application, this provides utility. For example, where one wishes low power consumption and a very flat load line to provide large voltage drop changes across the load resistor $R_L$, as shown in FIGS. 4 and 5, a small value of W/L is desired. Channel conductance is controlled by channel doping and back gate bias.

FIG. 2A shows a biochemical sensor 35 with a small W/L ratio. The width 37 of a conducting channel 39 is small relative to the length 41. A source 43 is connected to the channel 39 opposite to a drain 45. The small W/L ratio causes the sensor 35 to go into saturation at very low drain voltages, see FIG. 4. This ensures that the measurements are made in the saturation region, which can provide higher measurement sensitivity.

FIG. 2B shows a small W/L channel biosensor 47 using a meander line. A long channel 49 from source S 51 to drain D 53 is created in a compact region to cause the saturation of the sensor to occur at a low drain voltage.

There is a trade off in sensitivity for low W/L values compared to higher values. Selection is generally made under consideration of application and target signal strength. Incorporation of the W/L value in the FET analysis provides the sensitivity details that are considered in various tradeoffs.

A selection of intermediate values of W/L may be advantageous depending on the applications. For example, the saturation condition provides the highest trans conductance values. However, current levels are affected by W/L selection and must be kept within operational constraints (instrumentation and circuit measurement limitations) and power dissipation considerations. The sensor may be adjusted with respect to the $V_D$ value for the onset of saturation by adjusting the value of the back gate bias $V_{BG}$.

Doping levels. The channel doping determines the initial channel conductance. Back gate bias is used to modulate this channel conductance and to achieve sensitivity tunability.

Sensitivity tunability. By applying back gate bias, the channel conductance, determined by the number of free carriers available in the chancel, is controlled. The relative influence of the attached biochemicals is dependent on the number of free carriers in the channel. A lower channel free carrier concentration undergoes a large percentage change with attachment of charged biochemicals to the top gate. Thus, the back gate bias can be used to control the detection sensitivity of the sensor.

Back gate depletion. By adjusting the voltage applied to the back gate, the depletion encroachment on the conducting channel is controlled. This controls the sensor sensitivity.

The present invention also provides an integration of biosensors with a pH sensor, a temperature monitor, and an integrated heater. The chip system of the present invention provides superior performance and enables on chip control of PCR when desired and or temperature control when sensor measurement requires it.

The present invention includes integration on chip of two or more of the following components: one or more biosensors, a temperature measuring sensor, a pH measuring sensor, a resistive heater, and a temperature feedback control system.

The temperature of a sensor can affect chemical reaction rates and sensor electrical characteristics. Knowledge of the temperature may be an important parameter in providing accurate biosensor measurements. For example, any sensor temperature dependence that creates measurement error is undesirable. If a chemical reaction rate influences the sensor transient output, then the value of an influencing temperature should be known to accurately characterize such reaction rates.

pH affects the charge on biochemicals. A biosensor measuring charge provides a more reliable measurement and accurate relationship between sensor output parameter measurement and the number of molecules attaching if the relationship between pH and charge as well as the pH value is known.

One or more semiconductor pH sensors, or a new type of pH sensor, may be integrated on chip.

A resistance heater integrated on chip with a feedback control circuit that monitors and adjusts the measured temperature may control a temperature of the biochemical sensing chip by controlling the heater power to maintain a pre-selected temperature value. Temperature may be controlled and cycled where one wishes to affect nucleotide compound melting and/or PCR, or other useful biochemical function.

The present invention includes the integration of a temperature monitoring device, a pH sensor, a heater, a feedback system, and/or one or more biosensors all integrated onto a single chip. This system may be integrated with biosensors in arrays or single embodiments, and together with still other devices.

Figure 7:
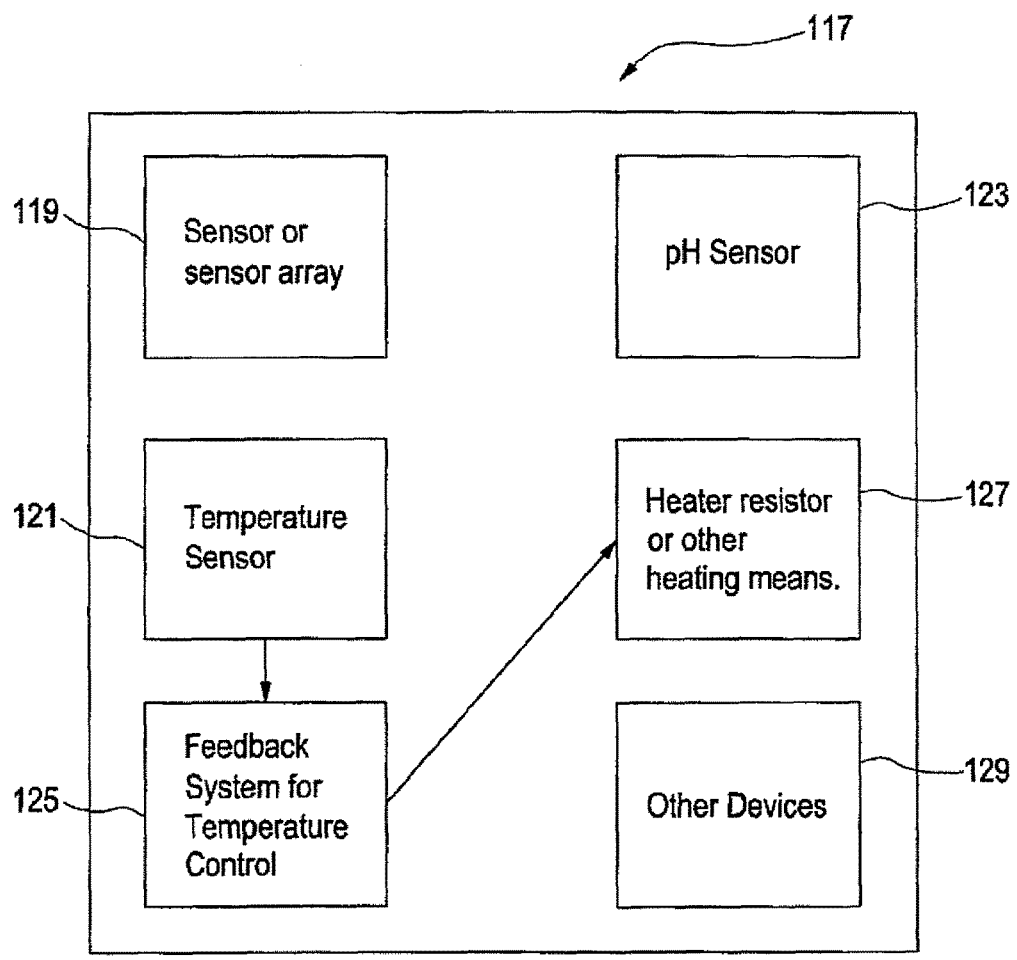
FIG. 7 schematically shows an integrated chip with temperature and pH sensing, and a temperature control system.

FIG. 7 schematically shows an integrated chip 117 with temperature and pH sensing, and a temperature control system. The integrated system 117 includes a sensor or sensor array 119, a temperature measuring device 121, a pH sensor 123, a feedback system for temperature control 125, a heater resistor or other heating means 127, and possibly other devices 129.

Silicon based simple electrical biosensing structures provide sensitive biosensing detection means with ease of measurement. Measurement instrumentation is off the shelf, low cost and easy to use. Non-engineers, such as biologists, pathologists and medical personnel, can easily perform the biosensing measurements. The biosensors are suitable for, but not limited to, Ab, oligo, RNA, protein and other recognition elements attached to the sensor surface. The recognition elements provide specificity. The sensors measure target chemical attachment influences sequentially. For example, proteins, viruses, c-DNA and other targets may be detected and quantitatively measured. A simple electrical output parameter provides the sensor measure of attachment. The sensors are easily fabricated as discrete sensors or as sensor arrays incorporating chip integrated addressing circuitry. Computer aided and automated diagnostics are supported by the inventions.

Biochemically sensitive silicon based resistors are fabricated and used to address biosensing and chemical sensing needs. Multiple applications including disease diagnostics for human, plant and animals are possible with these bioresistor sensors. The resistors comprise either an electrically isolated epitaxial layer or a polysilicon or crystalline layer, or other conducting layer. The resistors are doped and patterned to a geometry to provide a pre-selected resistance and detection sensitivity range.

Several benefits are realized, such as an appropriate value of resistance suitable for low cost instrumentation measurements, an appropriate doping concentration needed for best sensitivity for the application, geometries and resistance values best suited for sensor arrays with addressing circuitry, measurement circuitry and A/D conversion on chip, digital output best suited for subsequent information processing and instrumentation management, for example, visual alphanumeric readouts, and array configurations suitable for improved target identification and quantification reliability and simultaneous multiple target detection.

The polysilicon bioresistors are separated from an underlying substrate by a suitable overlaying insulator such as $Si_3N_4$. $SiO_2$ may be used to reduce surface state density. Top materials may be selected to provide a desired pre-selected contact potential and subsequent influence on the resistor's surface, and/or recognition element attachment compatibility.

Either epitaxial or polysilicon resistors are protected by an insulating coating above the bioresistor elements. Recognition elements are attached to the sensor surface. These recognition elements provide the binding site and mechanism for pre-selected target species identification and quantification. Specificity is provided by the recognition element.

High detection sensitivity enables multiple recognition elements to be placed on a single bioresistor thereby enabling sensing of many different targets by the same single sensor element. For example, in medical diagnostics one may sense for the presence of any one of many possible diseases. If any of the diseases are present, a signal is generated and further diagnostics efforts can be applied to isolate which of the diseases the patient has. The sensor in one embodiment preferably senses attached biochemical charge. Chemical contact potential changes (Gibbs free energy) can also be measured. Biochemical charge attached to the surface of the resistor causes an opposite charge change in the resistor. Such changes the resistance since the number of conducting charges is changed. Thus, the bioresistor's resistance value is changed in response to charged biochemical attachment. Resistance is measured. The resistance change provides a measure of target detection. A simple formula is used to determine the precise amount of charge attached to the sensor's surface.

Special configurations suppress unwanted moisture influences effects common to integrated circuit based devices.

The sensors are easily configured into arrays with addressing circuits placed on the same Si integrated circuit chip. Array applications include, but are not limited to, Genomics and Proteomics. For example, antibodies to various influenza types are incorporated and SARS is discriminated from other viral infections.

Applications are numerous ranging from medical diagnostics to homeland defense. Low cost instrumentation, such as an ohmmeter, provides for ease of measurement by non-technical individuals.

There are semiconductor IC active biosensor device obstacles that need to be overcome in semiconductor based biosensors.

Moisture influence on IC active devices is known to be adverse to semiconductor device performance. Biosensors typically are immersed in a liquid having a water component. This combination of biosensing features dictates serious design considerations for semiconductor based biosensors.

One major obstacle for the use of integrated circuit devices, such as FETs, is that such devices typically display serious and adversely influencing moisture sensitivity unless special care is taken to prevent such unwanted influences. Such conventional approaches are often impractical or undesirable. Emersion in an epoxy or plastic package is not useful for biosensors. Hermetically sealing a biosensors blocks the necessary exposure to the target containing fluids. Moisture influenced drift creates an error in the integrated circuit active device biosensor measurement. Such errors are problematic. They directly limit practical measurement sensitivity. A primary problem with moisture in active semiconductor devices is related to influences on premature breakdown at high electric field locations such as the depletion region of an FET drain to channel contact. In particular, when an FET is operating in saturation, the moisture influence problem is particularly pronounced.

Reduced IC processing needs are important. Much more processing using advanced integrated circuit technology is required to create an active device than a semiconductor based resistor. Where semiconductor based bioresistors of the present invention are used, the resistor may be placed outside of the primary integrated circuit area that is protected against moisture influences by thick insulators and packaging materials. Certain conventional IC protection maybe used while still exposing the bioresistor's active sensor area appropriately. That is more difficult for other biosensing semiconducting devices. Further, this allows for circuit protective means to be employed. Such protective means prevent unwanted biochemical charge electric field influences outside of the pre-selected active biosensor area.

Contact potential effects are important. Contact potential arising from the Gibbs free energy difference of a layer above the sensor displays itself functionally as a voltage between the over layer and the underlying biosensing semiconductor region. The contact potential can thus also influence the charge transport in an underlying biosensor. The contact potential can be very useful sensing parameter in addition or separate from charge sensing. However, if the overlaying insulating region is relatively thick and needed in order to block moisture, then the influence of such contact potential on the bioresistors or other bio IC sensor is suppressed or minimized. Where charge sensing alone is targeted, a relatively thick insulator is needed.

Pertinent to dimensional features, to provide a clean Gauss' law electric field over most of the biosensors, the lateral dimensions of the regions overlaying the active sensor region must be a much smaller dimension that the lateral active area of the biosensors. This again points to not using semiconductor sensor regions of nanometer dimension (in either of the two surface directions). By way of example, if the overlaying insulator is 3000 Angstroms thick (or 300 nanometers), then areas of approximately the same or lesser dimensions cause inhomogeneous electric fields in the biosensing region. That hinders ease of accurate assessment of the binding molecule details, such as concentration and net charge.

For contact potential measurement, a thin insulator layer is typically needed for separating the material of interest to be measured from the conducting semiconductor or material. Since measurement of small changes in contact potential in a material may be desired (e.g., in materials characterization), the insulator above the resistor must be kept very thin where the contact potential influence is to be made large. While this is problematic for active IC biosensor devices such as FETs and BJTs, resulting in significant moisture influences, the moisture influence on the bioresistors is much less significant if they are properly designed and biased. A bioresistor in principle can do a better job of measuring contact potential associated with biolayer attachment than an active IC device if the bioresistors are properly designed and biased. The bioresistor of the present invention is designed, biased and measured in a manner to suppress moisture influences on these charge measurements.

Sensor dimensions are important. Sensor dimensions in general should not be in the nanometer range as this creates limitations on applications for multiple target recognition. And, the biosensor's surface preparation with pH and binding function groups is a desirable feature, as well as robotic spotting of liquid containing recognition elements specific to multiple and different targets. Lateral surface dimensions of the active sensing region on the order of one or a few nanometers are not generally compatible with highly localized robotic recognition spotting to predetermined locations and sensor areas.

Surface state adverse influences are important. Surface trap states at the interface between the top insulator and the polysilicon or epi-Si resistor area, if not eliminated, can be filled and emptied without of charge that is induced by the top attaching biochemicals. Trapped charges do not change the resistor region conductance and thus those charges induced by attached targets but trapped at the surface are not sensed by the bioresistor or other conducting elements. Therefore, it is important in the fabrication technology to eliminate surface trapping states between the top surface and the conducting region. This is accomplished by ensuring the fabrication processing and temperatures used reduce or largely eliminate such surface traps. $SiO_2$ layers above and below the poly-Silicon (and above the epi where epi is used) together with IC processing can virtually eliminate such traps through surface binding means.

Figure 8A:
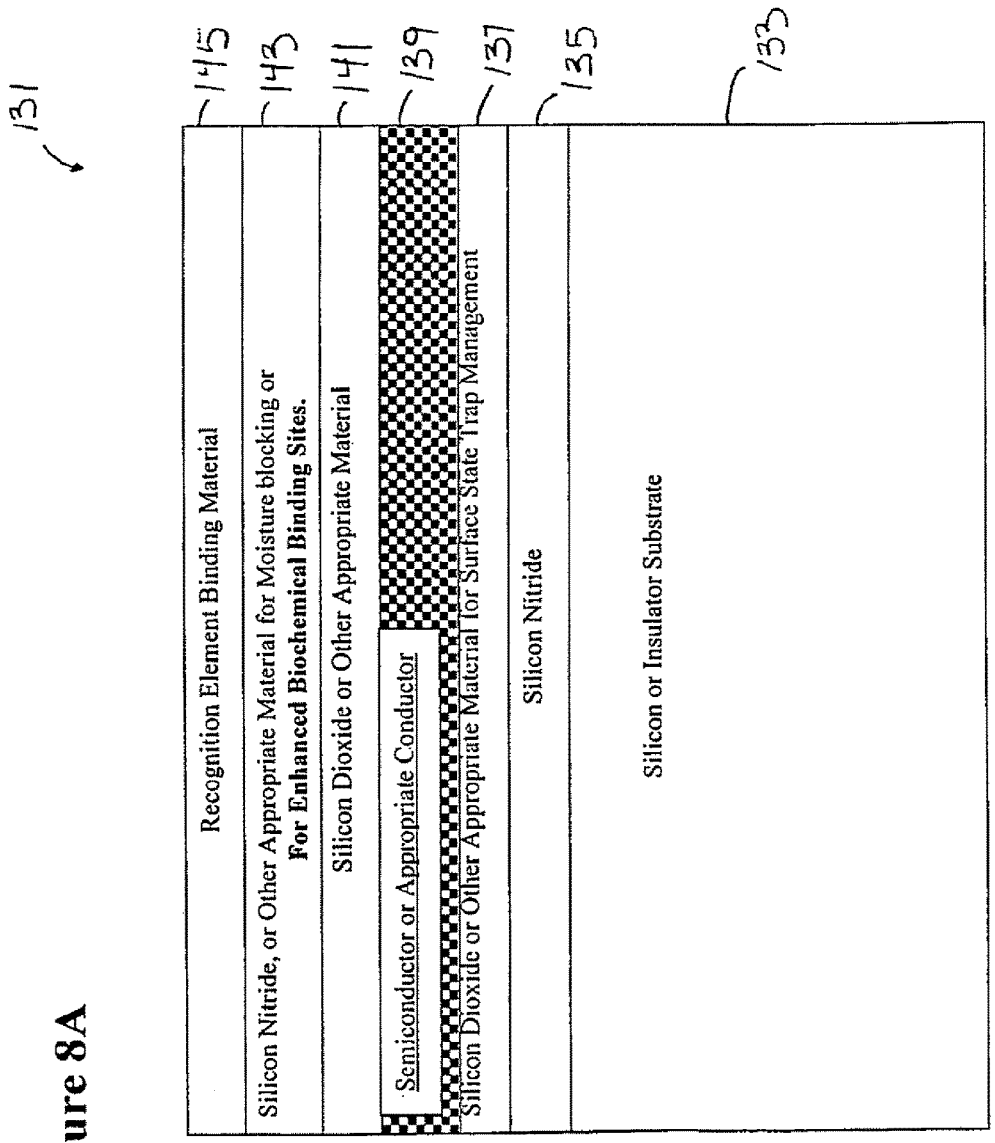
FIG. 8A shows a semiconducting resistor region.

FIG. 8A shows the basic structure for poly-Si resistors 131. A silicon or insulator substrate 133 functions as a base. Layers are added to the substrate 133 and include (added from the substrate 133 up) a silicon nitride layer 135, a silicon dioxide or similar appropriate material 137 for substrate state trap management, a semiconductor or appropriate conductor 139, a layer of silicon dioxide or other appropriate material 141, another layer of silicon nitride or other appropriate material 143 for moisture blocking or for enhanced biochemical binding sites, and a recognition element binding material 145. The $SiO_2$ does not need to be thick—a thin $SiO_2$ layer property fabricated, e.g. grown, suffices for such surface trap elimination. FIG. 8A shows a semiconducting resistor region. The semiconductor or other appropriate conductor is fabricated on a layer with minimum surface states. The supporting substrate 133 is floating. The sensing material may be Si, another semiconductor, a polymer, or a metal of other conducting material. The material may be crystalline or poly crystalline or disordered or amorphous. Subsequent figures do not show the surface state control layers, for simplicity of drawing.

Adverse effects of drain electric fields in FET structures are important. The drain of an FET is a location for high electric fields created by the PN junction effects of pinch-off. When such electric fields are present, moisture influences are particularly adverse. Premature breakdown and other measurement interfering phenomena may occur and introduce measurement error or erroneous sensor output signals. Such high electric fields are to be avoided and best eliminated from such biosensors that will be exposed to fluids.

Avoidance of pinch off and high electric field effects in poly and epi resistors is important. By floating the substrate for an epi resistor, the pinch off effect is avoided at high resistor voltage drops. This is because the pinch off effect results from a bias between the conducting channel and the substrate. Eliminating the substrate voltage bias, even eliminating a grounding of the substrate, avoids the high electric field effects and the premature breakdown. This avoids or suppresses any moisture sensitivity.

Insulator selection and insulator dimension selection is important. Further protection is accomplished by providing a suitable nitride coating above the resistor, as shown in FIGS. 1A and 1B. Such coating should be generally 2000 Angstroms thick or thicker to block moisture.

Past problems with biosensing devices intended to measure attached charged target biomolecules have been the effects of potential screening charges in the testing fluid, such as those ions contained in a buffer solution, partially or wholly shielding the target charge. When this influence is sufficiently strong as to shield the target molecules charge partially or wholly, the signal from the target charge may be partially or wholly canceled. This occurs because the target associated electric field is now from a lesser or zero charge or screened charge, and it is this electric field that influences the underlying bioresistor or charge sensor that is needed to influence the underlying bioresistor. Methods must be employed to reduce or eliminate the adverse shielding effects. Among these methods are pulling the sensor from solution, rinsing it with buffer, blowing lightly dry, and making the measurement, making the measurement in a largely non-ionic fluid, and applying a net repulsive voltage to the bioresistor sensor to repel unbound screening charges and quickly making a measurement when the screening charges have been removed.

The bioresistor of the present invention has many advantages including: relative moisture insensitivity, circuit compatibility, ease of physical measurement and instrumentation costs.

Circuit compatibility has several components. For RC oscillators, frequency is counted for a sensor output parameter. The change in resistance is proportional to the attached biochemical concentration. For time constant dependent circuits, for example, the rise or fall time of a pulse may be measured with the RC time constant controlling such rise or fall times. The capacitance C is a constant. Therefore, R and the change in R, <R, arising from biochemical influences are easily measured. Other more sophisticated circuits may employ a resistor and provide a measure of resistance change.

Ease of physical measurement is critical. The biosensors are to be used by biochemists, medical researchers, MDs and others. Most of these groups does not have a deep understanding of instrumentation, but can operate a conventional ohmmeter. Resistance measurement with an ohmmeter is simple.

Instrumentation costs are critical. Ohmmeters are relatively inexpensive and provide high performance. The best current ohmmeters can measure resistance to close to 6 significant figures. Very low cost ohmmeters can easily measure to 3 significant figures. Thus, measurement of resistance change provides resolution to 0.1% to approximately $10^{-4}\%$.

The present invention is understood in terms of the attached Figures and Tables. The present invention includes a semiconductor or other conducting resistors designed to provide sensitivity to attached chemicals, especially biochemicals, or particles that carry charge. The charged molecules attach specifically to recognition elements that in turn are attached to a region of the biosensors that enables them to influence the underlying or adjacent semiconducting or conducting region. One bound charge in principle provides one change in conducting charge of the opposite sign to the binding molecule's charge.

Figure 14:
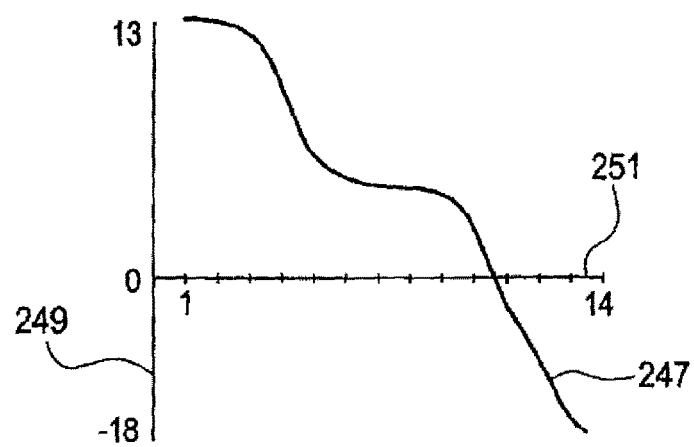
FIG. 14 shows a rabbit phosphorylase B isoelectric curve.

FIG. 14 shows a rabbit phosphorylase B isoelectric curve 247. Rabbit phosphorylase B is cheap, well behaved, large (lots of charge), a nice pI distribution centered around 6.75 vertical axis 249 is net charge. Horizontal axis 251 is pH.

Figure 15:
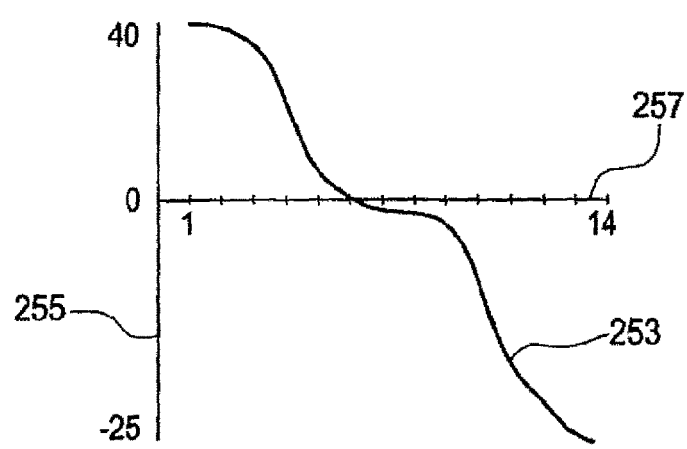
FIG. 15 shows an isoelectric curve for streptavidin.

FIG. 15 shows an isoelectric curve 253 for streptavidin. The charge (vertical axis 255) is plotted versus pH (horizontal axis 257) of the containing solution.

Figure 16:
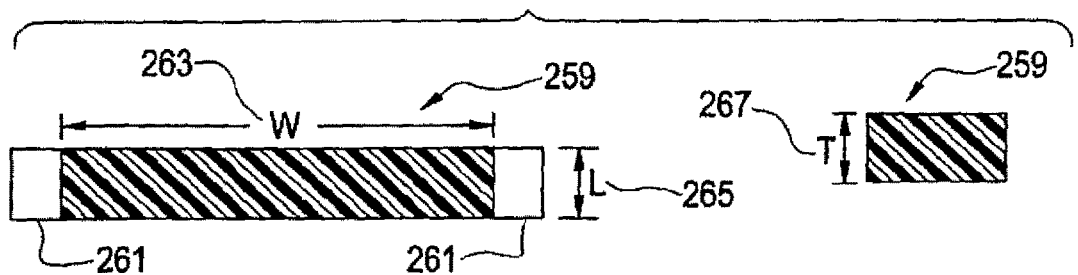
FIG. 16 shows a rectangular bioresistor.

FIG. 16 shows a rectangular bioresistor 259. The distance between a contact 261, W 263, the second lateral dimension L 265, and the thickness T 267 for a resistor 259 are shown.

The present invention addresses the use of semiconductor or conducting resistors for the purpose of biochemical sensing. Biochemicals have charge, as shown in FIGS. 14 and 15. Attachment of charges to the surface of a resistor sets up image charges that affect the free conducting carriers in the bioresistors. The change in free conducting charge in the bioresistors exhibits itself and a change in the bioresistors resistance. A measure of this resistance change provides a measure of the attached charge and therefore a quantitative measurement of the attach biochemical concentration.

Recognition elements are attached to the resistor surface to provide a specificity function. The recognition element ideally binds to a charged target molecule and only to that target molecule.

Such resistors are illustrated in FIGS. 8-13. The resistor indicated here, and the preferred bioresistors, are fabricated from semiconductors. Semiconductor resistors may be of poly-semiconductor material, of either carrier type, fabricated on an insulator. The semiconductor resistors may be fabricated using epitaxial semiconductor grown on a semiconductor of opposite carrier type to provide PN junction electrical isolation. Alternatively metal resistors may be used.

Figure 8B:
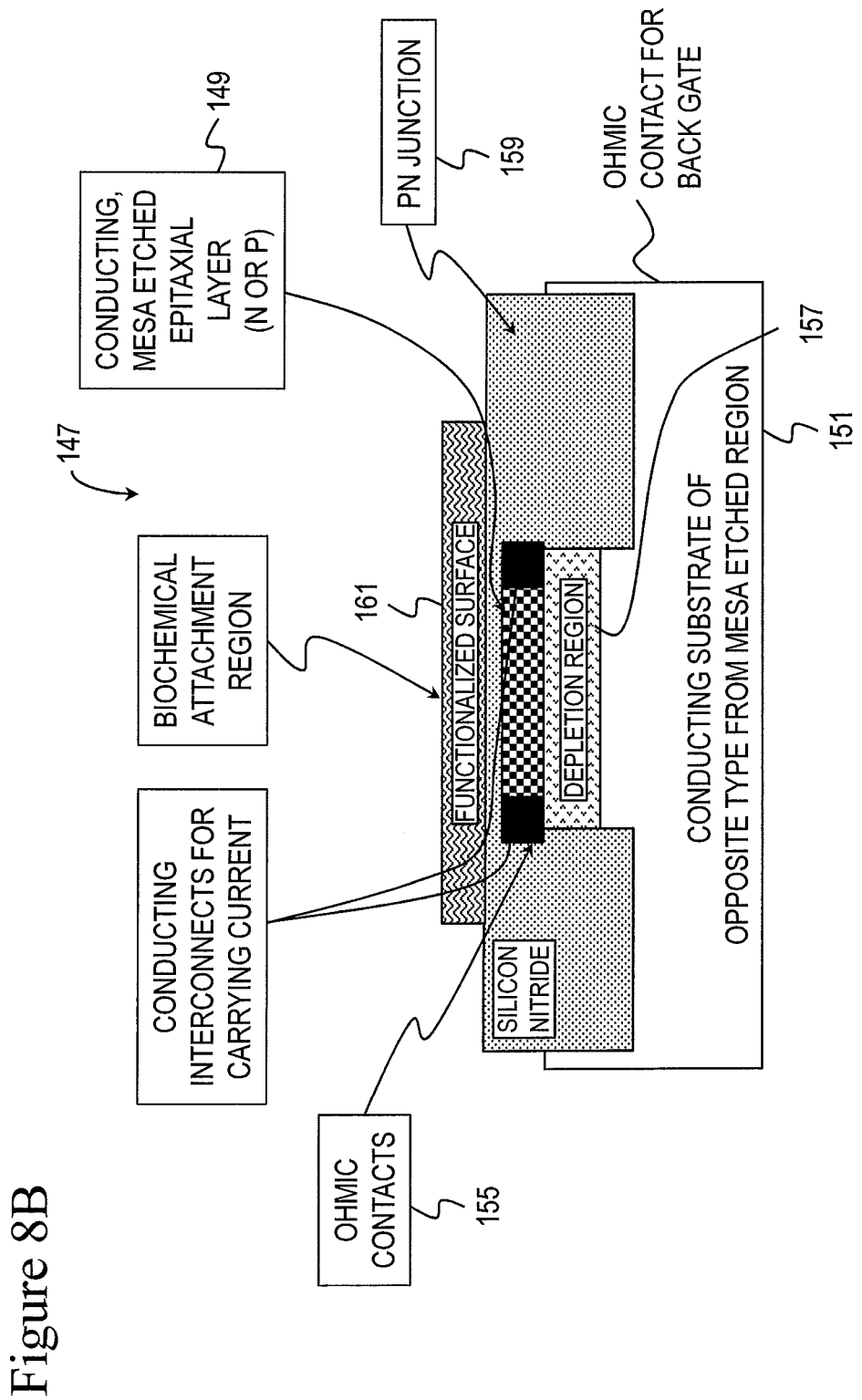
FIG. 8B is a cross sectional view of an epitaxial resistor.

The resistors may be created using integrated circuit (IC) technology in various ways. By way of example, two types of resistors are shown in FIGS. 8A, 9A-9E and FIG. 8B. Polysilicon resistors fabricated on insulators and epitaxial semiconductor resistors are shown in FIG. 8B.

Figure 9A:
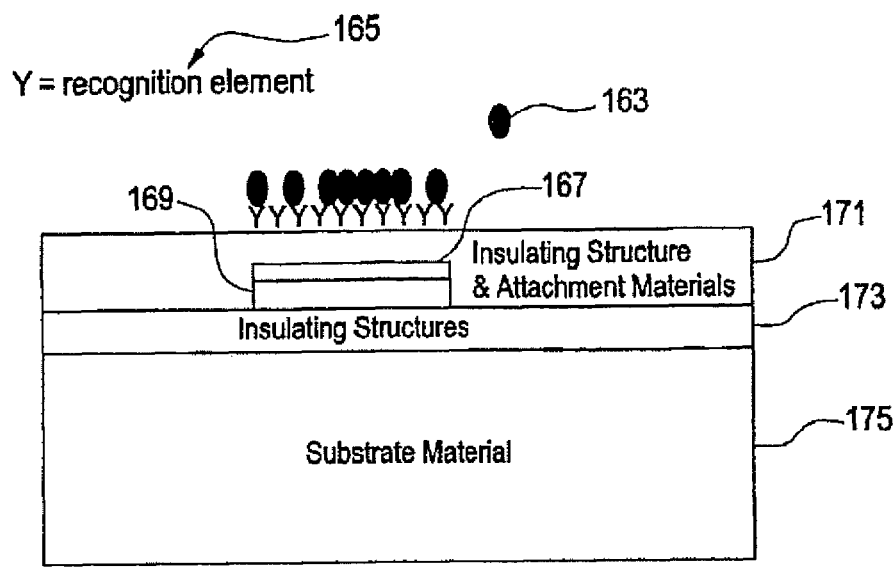
FIG. 9A shows targets binding to recognition elements.

FIG. 9A shows targets 163 binding to recognition elements 165. An insulating structure and attachment material 171 surrounds a resistor 167 and depletion region 169. The resistor 167 is located on an insulating structure 173 that is located on a substrate material 175. When the targets 163 bind, their charge and/or contact potential influence the underlying concentration of holes or electrons in the resistor. For negatively charged targets, a whole doped resistor (P-type) experiences an increased resistor free carrier concentration and thus a decreased resistance. An electron-doped resistor in this example would experience a reduced electron concentration in the resistor with a subsequent resistance increase.

Figure 9B:
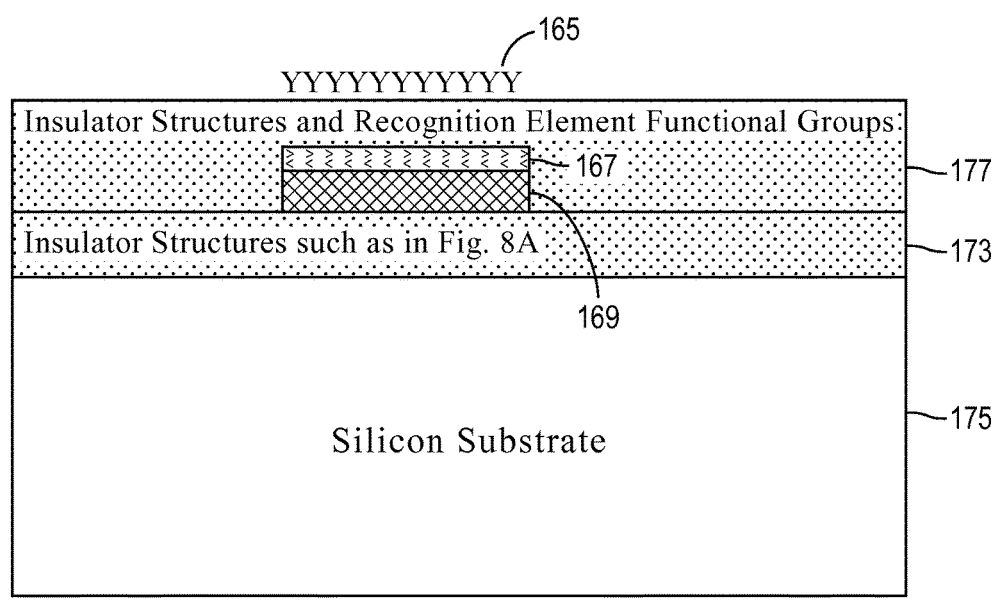
FIG. 9B shows recognition elements attached to a resistor gate region.

FIG. 9B shows recognition elements 165 attached to a resistor gate region. The resistor 167 is surrounded by insulator structures and recognition element functional groups 177. The charges associated with the recognition elements or target molecules can deplete some of the current carrying charges in the resistor, thereby raising the resistance.

Figure 9C:
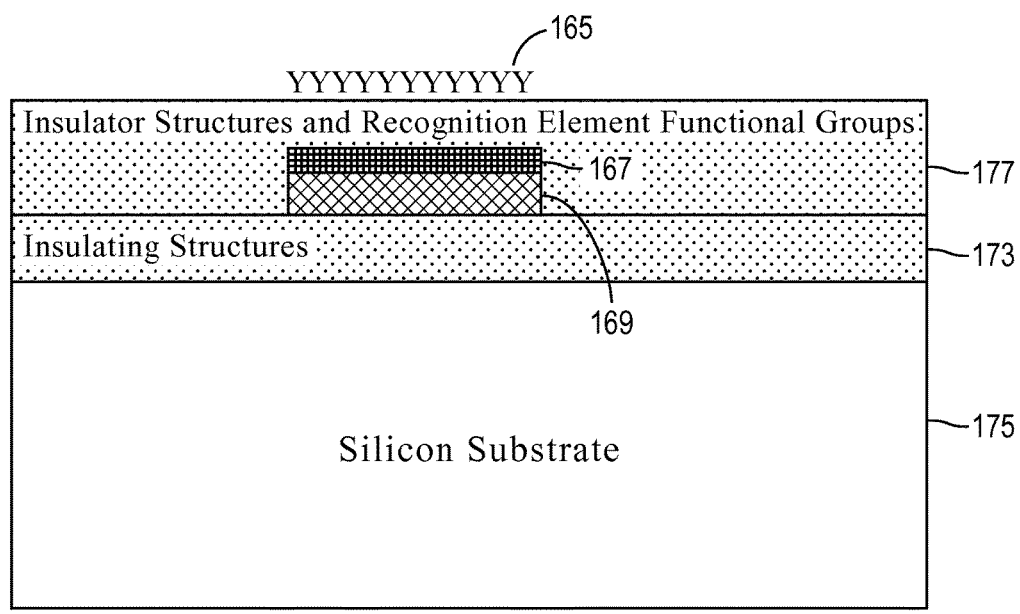
FIG. 9C shows recognition elements attached to a resistor gate region causing accumulation.

FIG. 9C shows recognition elements 165 attached to a resistor gate region causing accumulation. The charges associated with the recognition elements or target molecules can attract carriers to the resistor (accumulation), thereby lowering the resistance.

Figure 9D:
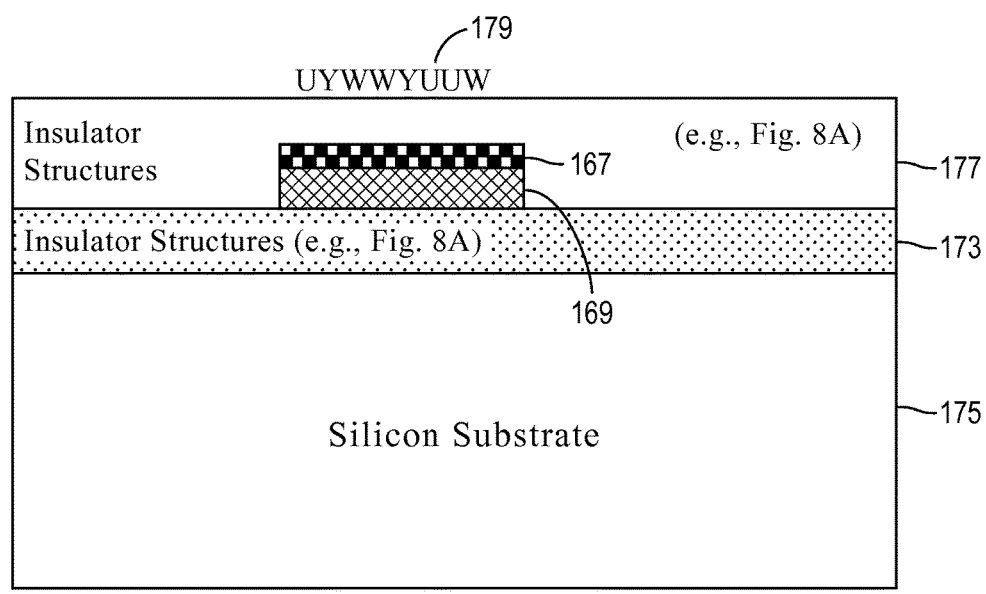
FIG. 9D shows multiple recognition elements attached to a resistor gate region.

FIG. 9D shows multiple recognition elements 179 attached to a resistor gate region. Multiple recognition elements 179 (Y, U, W, V) are attached to the resistor surface 167 in order to test a sample of the presence of any one or more of many targets present.

Figure 9E:
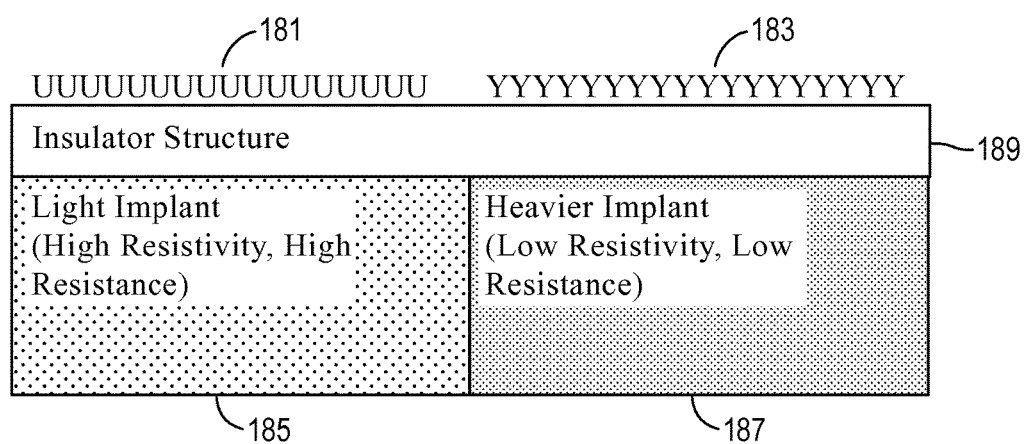
FIG. 9E shows a polySi resistor with multiple detection targets.

FIG. 9E shows a polySi resistor with multiple detection targets 181, 183. One set of targets 181 is located over a light implant 185 with high resistivity and high resistance. Another set of targets 183 is located over a heavier implant 187 with high resistivity and low resistance. An insulator 189 separates the implants 185, 187 from the targets 181, 183. By selectively doping with implants or predeps different regions of the bioresistor, one can selectively address (1) different targets, (2) different target concentrations, and (3) multiple sensing objectives. Recognition elements may be attached in pre-selected geometric regions using patterning techniques, optical assisted binding and patterned binding materials.

For epitaxial resistors, a conductive region of a different type (e.g. N) than the underlying wafer type (e.g. P) is created. The resultant PN junction is thus electrically isolated from the bulk substrate. Silicon is used for the preferred semiconductor in this discussion. However, other semiconductors may be used.

FIG. 8B is a cross sectional view of an epitaxial resistor 147. A Si epitaxial layer 149 is deposited on a Si substrate 151 and subsequently isolated and defined using mesa etching technology. The conducting substrate 151 is of an opposite type from the mesa etched region. A depletion region 157 is located under the conducting, mesa etched epitaxial layer (N or P) 149. Ohmic contacts 155 surround the epitaxial layer 149. A PN junction 159 is made of silicon nitride. A functionalized surface 161 is located over the PN junction 159. The resistor has a back gate that can be used to modify the concentration of carriers in the resistor. This device is different from a conventional FET. It is intended to be a resistor where only the resistance is measured. The epi is doped with a different type (N or P) than the substrate (P or N, respectively) to provide electrical isolation. Additional insulators (SiO2) are not shown for ease of viewing.

The top conduction region 153, as shown in FIG. 8B, in this example (N type) may be formed on the Si substrate 151 (P type example) by epitaxial grown and doped with ion implantation or predep incorporating diffusion and other various means known to those in the IC technology art. The epi bioresistor is then defined in FIG. 8B using a mesa etch technique. Electrical contacts 155 are applied as they would be for an IC device with a $N^+$ contact (N resistor example) at either end to provide ohmic introduction and removal of current.

A polysilicon bioresistor is shown in FIGS. 8A, 9A-9E and 10A, B and C. Here a polysilicon layer is grown on an insulator. The resistor may be fabricated with various shapes in order to control its resistance, as shown in FIGS. 10A-D. The poly-Si resistor is patterned using etching methods to provide geometry of interest. Examples are shown in FIGS. 10A-D. The parameters determining the resistance are the resistor length, width, thickness, doping concentration and type (N or P). The polysilicon is grown on the surface of an insulator such as $Si_3N_4$ or $SiO_2$ to isolated it electrically from the underlying substrate. The substrate may be of Silicon, aluminum oxide, or some other insulator. Si is a preferred substrate.

Figure 10A:
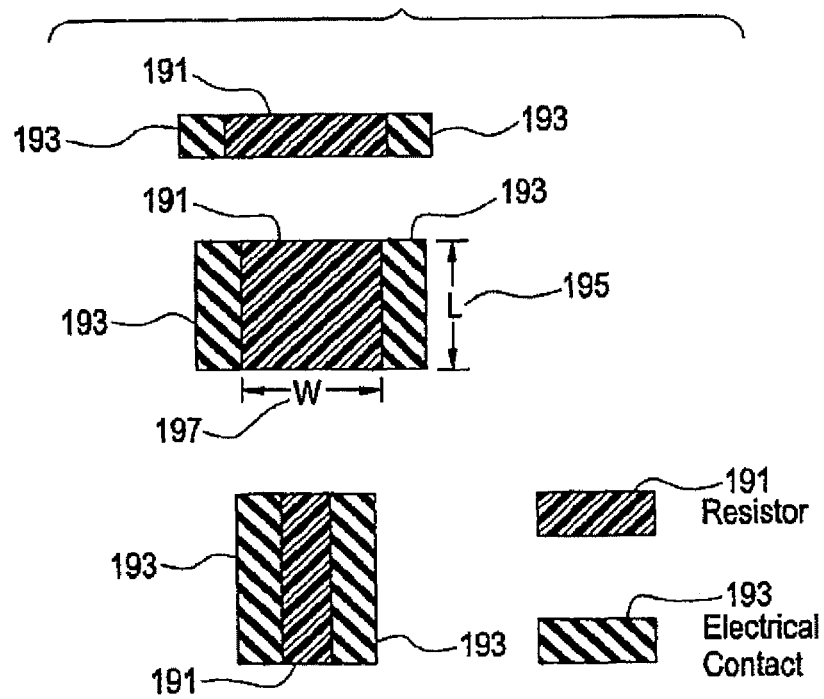
FIG. 10A shows resistor geometries.

FIG. 10A shows resistor geometries. A resistor 191 is surrounded by an electrical contact 193. The resistor 191 has dimensions L 195 and W 197. Resistor geometries may take different shapes, as indicated.

Figure 10B:
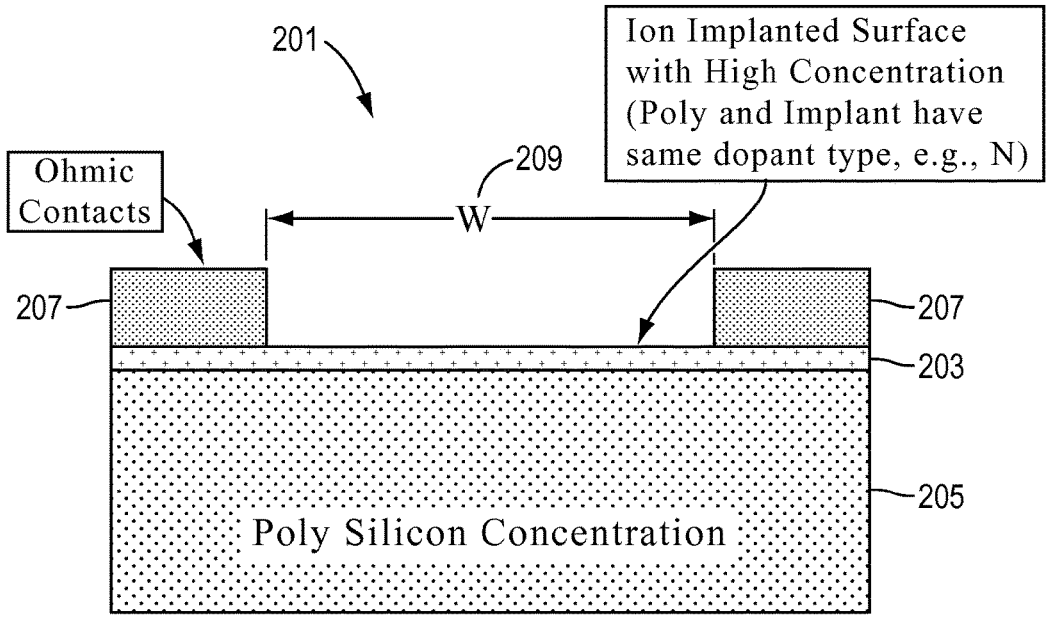
FIGS. 10B and 10C show an ion-implanted resistor on polysilicon.
Figure 10C:
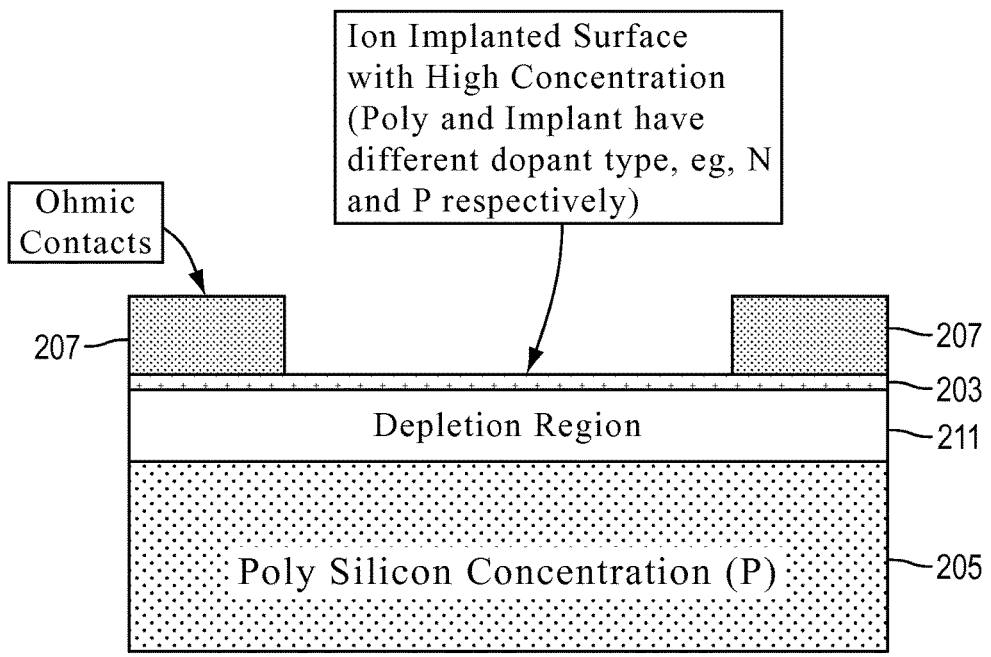

FIGS. 10B and 10C show an ion-implanted resistor on polysilicon. Insulators present above and below are not shown. FIG. 10B shows a poly resistor 201 with an implant of dopant of the same type as the background polyresistor doping. A conductor 203 is located on a substrate 205. Ohmic contacts 207 are separated by a width W 209. An ion-implanted surface has a high concentration. The poly and implant have the same dopant type, e.g. N. FIG. 10C shows an implant of dopant opposite in type to that of the polysilicon background doping, thus providing a PN junction isolated top resistor layer on the polysilicon. A depletion region 211 forms between the substrate 205 and the conductor 203. The resistance of the implanted resistor is measured via the ohmic contacts made to the implanted layer.

Figure 10D:
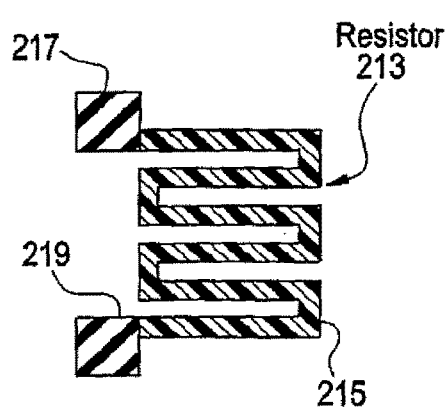
FIG. 10D shows a meanderline resistor.

FIG. 10D shows a meanderline resistor 213. A meanderline 215 connects a first contact 217 to a second contact 219. Where a higher resistance is desired, a meanderline resistor is constructed from epitaxial material as a mesa features, as a diffused or implanted region in the substrate, as an SOS structure, as a polysilicon structure, or as hetero structure. For biosensor structures, the separation between arms of the meanderline is typically kept small.

Poly-semiconductor, such as polysilicon, resistors may be grown in $SiO_2$, sapphire, or other insulating substrates.

Electrical ohmic contact connections are made in the way usually employed for a semiconductor device. These methods are either heavy doping resulting in a tunneling ohmic contact or suitable alloying (e.g., Al on P—Si).

The geometry is chosen to provide a pre-selected resistance most suitable for the measurement of interest and/or for circuit integration. The longer the resistor, the higher the resistance. The wider the resistor, the lower the resistance. The thinner (T) the resistance, the higher the resistance. The lower the doping concentration in the resistor, the higher the resistance. Tables 1-3 show various features of resistors doped at different concentrations using the resistively as the measure of the doping concentration. The resistor may be characterized in Ohms/▱ for convenience. This parameter used in the usual way to determine the total resistance. Meanderline resistors may be constructed to provide resistance with a compact active sensor area, as shown in FIG.

10C. Resistors of differing dimensions and electronic structure, as shown in FIGS. 10A-D, may be selected to address applications specifications including resistor values.

Resistor carrier concentrations and sensitivity considerations are important. The bulk free carrier concentration can be viewed from a top down perspective and the carrier concentration converted to a concentration per $cm^2$ or per $\mu M^2$. Tables 1, 2, 3 and 4 provide some illustrative examples for bioresistors either using epi or implanted polysilicon or implanted bulk resistors. This surface density parameter is used in the resistor design. There is a surface density of recognition elements and subsequent bound target molecules. These translate to a surface charge concentration above the resistor that is reflected in a like change in the resistors free charge and thus it resistance. Typically biochemicals are of small dimension and in principle a large number of recognition elements (such as antibodies or oligos) can be attached to the surface in a square micron. The percentage influence of the biochemical charge on the underlying semiconductor free charge provides a direct measure of the percentage change in the resistor.

Sensitivity considerations are critical. By way of example, consider the implant doses in Table 2 provided information that can be used to indicate the biosensor's sensitivity. At one ohm-cm, the concentration is $5.5 \times 10^3/\mu M^2$. Thus, if 500 antibodies capture targets with 2 charges each, there is an approximate resistance change of 20% or 2K in an N-type 10K square bioresistor. This is easily measured with low cost ohmmeters. Such a concentration of targets per $\mu M^2$ is quite reasonable. If one moves to 30 ohm cm material, the same percentage change occurs with approximately 17 targets binding. Higher resistively material or thinner resistors provide even more sensitivity. Quality ohmmeters measure with a resolution of nearly $10^{-6}$. This translates to a bioresistor sensitivity of less than 1 electrical charge (positive or negative) per $\mu M^2$. If there are 1000 Ab per micron equate, that is 1000 charges. Indeed, only a few of the antibodies need to be bound to a target to be detected. For example, with this sensitivity, botulinum toxin should be detectable at lethal doses. High-density recognition element attachment can be affected using other techniques.

Polysilicon and epi bioresistors with different sensing regions are possible. Using patterning technologies, the bioresistor is made to incorporate multiple sensing resistor regions for different targets. One target may be present in high concentrations levels if the target is hazardous. Other targets may have low concentration hazard levels. Differing concentrations for different targets is affected through geometrical patterning of the resistor doping, as shown in FIG. 9E. Polysilicon resistivities are approximately twice that of bulk Si for the same doping concentrations.

Biosensing bioresistor arrays are possible. The poly Si and mesa etch semiconductor bioresistors sensors are easily patterned into large biosensor arrays. Analog and digital addressing circuitry can be integrated on chip. Such arrays have significant utility in providing sensing simultaneously of multiple identical or different targets with high sensitivity and ease of measurement.

Figure 11:
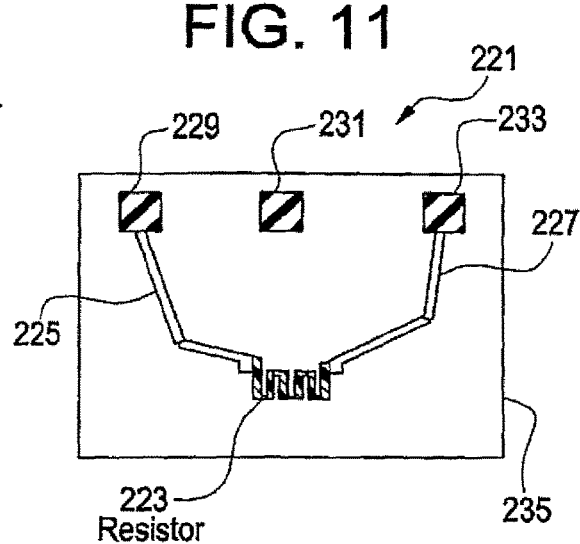
FIG. 11 shows a biosensing resistor chip.

FIG. 11 shows a biosensing resistor chip 221. A meanderline resistor 223 is shown together with electrical interconnects 225, 227 going to contact pads 229, 231, 233. Three contact pads are shown on a substrate 235. The central one 231 may be connected to a PN isolation junction on a diffused or epitaxial resistor for tunable sensitivity.

FIGS. 14 and 15 provide isoelectric information for streptavidin and a mouse protein. It is noted that at pH 7.0 the net charge per molecule is significant. The net charge changes with pH indicating the bioresistors may be used as pH sensors. Further, the charge change with pH can be used to access confirmatory identification information for a target. In another example, botulinum toxin has a net charge of about 15+/−3. Viruses are charged. Bacteria are charged. The epitopes of bacteria and viruses are charged. Antibodies are charged. DNA has two negative charges per base pair. Oligos and single stranded RNA have one charge per base. DNA and RNA have many bases and thus are heavily charged. Such charge can be detected using the bioresistors of the present invention. The bioresistors may be used in arrays to provide gene chips, proteomics chips, confirmatory RNA information, and other information.

Sensor chip circuit integration is possible. The underlying wafer may provide integrated circuit connections for electronic function. Such IC devices are not shown for simplicity, but it is understood that they may be present and are particularly useful where chip integrated sensor arrays are fabricated for multiple targets, as shown in FIG. 12.

Figure 12:
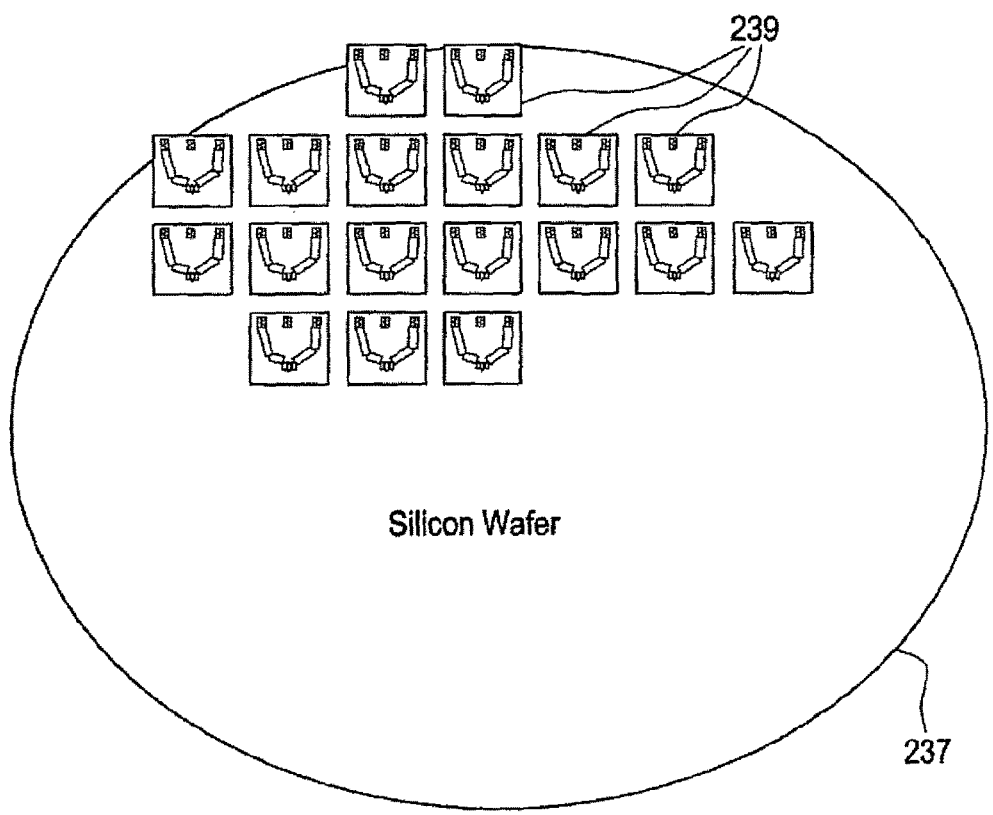
FIG. 12 shows a silicon wafer with a batch of bioresistor sensors.

FIG. 12 shows a silicon wafer 237 with a batch of bioresistor sensors 239, as shown in FIG. 11. Batch processing is used to manufacture low cost bioresistor sensors. Only some of the chips are shown.

Figure 13:
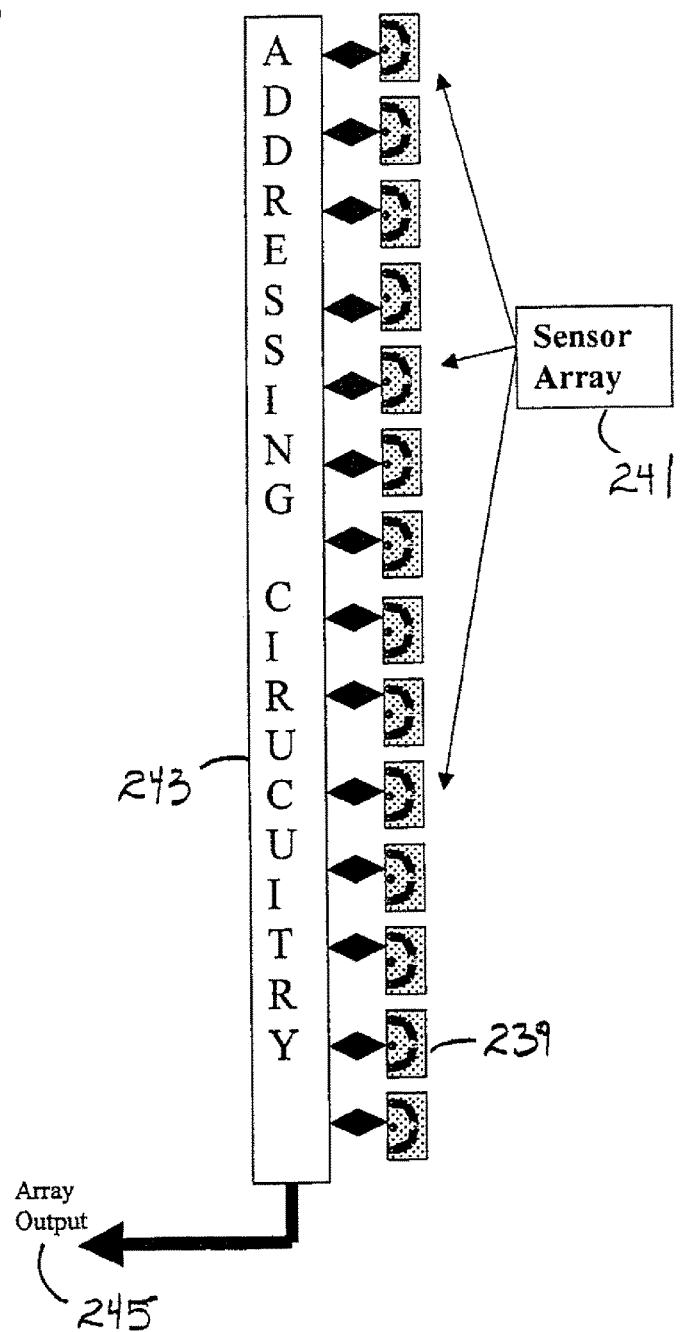
FIG. 13 shows an integrated sensor array with addressing circuitry.

FIG. 13 shows an integrated sensor array 241 of bioresistor sensors 239 with addressing circuitry 243 and an array output 245. A one-dimensional array with addressing circuitry is schematically represented. A two dimensional array of biosensors can also be incorporated with similar addressing circuitry. The circuitry includes A/D conversion and signal management circuits.

Low cost biosensors and batch processing are possible. The Si based sensors are easily batch processed using standard integrated circuit techniques. Large wafers and small sensors, due to high sensitivity, may be used to provide very large numbers of sensor chips in a single run, thereby providing very, very low cost sensors. For example, a 6-inch wafer can easily provide 1000 sensors, more if chip size is reduced to the maximum practical.

Arrays are easily processed simultaneously. An array of 10×10 on the same chip is easily fabricated together with hybrid outputs or integrated addressing circuitry.

Bioresistor measurement techniques are provided. The sensor is measured using an ohmmeter or circuit with a resistance value dependent output, such as an RC oscillator. In the latter, frequency output and output change is measured.

The Bioresistor is designed with the needed sensitivity in mind. The following equations may be used conveniently to design the resistors.

$$R = R_\rho \times L/W \cdot T \text{ (spatial dimensions in microns)} \quad (1)$$

$$N_\rho (/\mu M^2) = \ell \times T \text{ (microns)} \quad (2)$$

Two main issues are involved: (1) the values of resistance such that the resistances are easily measured using conventional test equipment, and (2) the doping concentration that is important in determining the <R/R, the sensitivity. Here <R is the change in resistance arising from the attachment of biochemicals to the surface of the resistor.

Using the basic equations and information in Table 1 and Table 2, the value of <R/R is easily calculated. From a percentage point of view, Table 1 shows the resolution with a quality ohmmeter having a resolution of <R/R=$10^{-5}$. By way of example, for 10 ohm-cm N type material, one can thus measure a change of one electronic charge per square micron. Typically this would be better than one molecule/ square micron. Since the biochemicals of interest are typically much less than 1 square micron in dimension, one would expect many recognition elements in one square micron. If twenty-five base pair oligos were used, then binding would provide 25 charges/oligo. Many oligos would be bound to a single square micron. Other examples can be calculated or designed using equations (1) and (2) and the information in Tables 1, 2 and 3.

Even infrequent binding event are measured with an easy resistor design. That translates to very high sensitivity.

Polysilicon bioresistors are fabricated using technologies commonly accessible in integrated circuit manufacturing foundries. The semiconducting region is separated electrically from an underlying supporting substrate. Polysilicon resistors are well known in the IC fabrication art. However, special designs are needed to create a bioresistor. Furthermore, the fact that a resistor can be structured to incorporate both recognition elements and binding targets that can influence the underlying conduction by image charge modification of the conductivity is needed. Resistance by itself is not the issue. It is necessary to create a bioresistor that has suitable sensitivity to the biochemical or other chemical or material target of interest. Either chemical target charge or material contact potential can be measured.

Anti-charge trapping configurations are possible. Surface state charge traps can reduce or completely blunt the biosensing function. The top surface of the poly-Si should be free from traps and charge trapping so that the modulation of charge by the attached biochemicals is only or mostly modulation of mobile charge concentration, and not filling and emptying of trapped charges sites. This is accomplished by incorporation of suitably formed silicon oxide level on top of the resistor Si, as shown in FIGS. 8A and 8B. Surface states may empty or fill with charge without affecting the resistivity of the biosensing resistor. Such behavior results in no bio-resistance change with attached recognition element or targets. This is accomplished in several ways. First, the poly Si top surface is coated with an oxide thermally grown in a manner to minimize surface states and trap interface states. Such techniques are well known in the IC manufacturing art. Second, the top surface of the poly silicon is doped and selected such that the top surface is in accumulation. This is affected by selection of the doping, doping type and top insulator.

Accumulation and depletion are important. The surface attached biochemical charge can either increase the concentration of conducting charges in the resistor or decrease the conducting charge area concentration. Which occurs depends upon the charge sign of the target and of the free conducting carrier in the bioresistor. Accumulation and depletion may normally occur depending on resistor carrier type and concentration, and density of attached charge.

Inversion is important. Doping the semiconductor and applying ohmic contacts enable attached target charges to modulate the surface concentration in an inversion region. In such case, the ohmic contacts must be ohmic to the inversion charge type. If a conductor (bioresistor) of particular charge carrier has ohmic contacts (e.g., $P^+$ to a P-type resistor), and the surface is inverted (to N type), the modulation of the inversion region by subsequent target charges will not be measured due to PN junction formation. This situation is to be avoided in the sensor design.

For epitaxial bioresistors, similar considerations apply to design and manufacture of epitaxial resistors. Key features include epitaxial types, epitaxial doping concentration, epitaxial thickness, and incorporating multiple recognition elements for multiple target sensing. Epitaxial type is opposite to the substrate type in order to provide electrical isolation. Epitaxial doping concentration shows that low doping translates to higher detection sensitivity. Epitaxial thickness shows that the thinner the epitaxial layer, the lower the total free carrier concentration per square micron, and the more sensitivity the device to charges attached to the top region. Incorporating multiple recognition elements for simultaneous multiple target sensing is important. With such sensitivity, it is easy to put multiple different recognition elements on a single bioresistor and test for the presence of many different targets in the sample simultaneously. FIG. 9D shows such multiple recognition element incorporation by way of schematic example.

Recognition element attachment methods are used. Recognition elements may be attached to the surface of the resistor using technologies available now, or which may be developed in the future. For example, the top insulator protecting the resistor may be coated with a polymer to which binding of the appropriate chemicals is affected. Polystyrene is one example. Latex is another. Binding densities and binding strength may be improved with Silanization. Intermediate binding assist may be affected such as the attachment of streptavidin to the surface with the recognition elements being prepared with a biotin linked antibody or oligo. The biotin binds well to the streptavidin thereby providing the bound recognition element required for specific target binding.

Recognition element density is important. In theory, recognition element density may be such that approximately every 10 Angstroms has another recognition element. This translates to approximately $10^6$ recognition elements, such as antibodies or oligos, per square micron. In practice, the recognition element surface density will be less than $10^6$ per square micron.

Bioresistor sensitivity of measurement is important. Even if the recognition element density is less than one, two or three orders of magnitude, the influence on a properly designed bioresistor can be large. Assuming only one charge per target is bound to a recognition element, at $10^4$ recognition elements per square micron, this would translate to $10^4$ charges per square micron. A 10 micron square, one micron thick epi resistor doped at $10^{13}/cm^2$ can be measured to approximately 10 electron/sq micron. Ohmmeters measuring one part in $10^3$ (0.1% resolution) can easily measure such a signal. Indeed, such a large signal may be much too large. This permits many different recognition elements to be located on the same 10 square micron epi resistor.

Several issues are relevant. First, high sensitivity of binding recognition elements is not required for achieving good sensitivities. Second, measurement of modest densities of binding events using a simple, low cost ohmmeter is easily performed with excellent resolution. Next, a resistor of nanometer dimensions is nether needed nor desirable. Next, partial shielding by buffer ions is overcome using techniques and high-resolution measurements with simple low cost ohmmeters.

Biochemical target measurement examples exist. Numerous combinations of recognition elements and targets can be imagined for biosensor applications. Multiple sequential measurements can be made to support various measurement objectives. The following are by way of a few illustrative examples: buffer influences, antibody attachment, anti-antibody attachment (e.g. rabbit antibody to mouse antibody), antibody to target, antibody/target/antibody sandwiches, oligo attachment, bead attachment, recognition element to target attachment, pH change of bound charge influences on the above, isoelectric points, particle attachment (charged or uncharged), chemical potential shift arising from attached targets, nucleic acid attachment, protein attachment, receptor attachment, recognition element attachment, and specific vs. non-specific attachment.

A testing method is provided for testing quasi dry. A problem reported for biosensing devices intended to measure attached charged target biomolecules in the past has been the effect of potential screening charges in the testing fluid, such as those ions contained in a buffer solution, partially or wholly shielding the target charge. When this influence is sufficiently strong as to shield the target molecules charge partially or wholly, the signal from the target charge may be partially or wholly canceled. This can occur since the target associated electric field is now from a lesser or zero charge (screened charge) and it is this electric field that influences the underlying bioresistor or charge sensor, which is needed to influence the underlying bioresistor. Methods must be employed to reduce or eliminate the adverse shielding effects. Among these are pulling the sensor from solution, rinsing it with buffer, blowing lightly dry, and making the measurement, making the measurement in a largely non-ionic fluid, and applying a net repulsive voltage to the bioresistor sensor to repel unbound screening charges and quickly making a measurement when the screening charges have been removed.

If the surface of the sensor is prone to non-specific binding, methods for blocking or reducing non-specific binding may be used.

Applications are diverse. Tables 6 and 7 provide an example listing of recognition elements and target molecules. The list is far from complete.

Since the net molecular charge is pH dependent, an appropriate biochemical bound to the bioresistor will have a pH dependent charge. By calibrating, one can use the invention in this mode as a pH monitor.

Sensor arrays may be used for multiple target detection and for gene chips, proteomics chips, drug discovery chips and more, see Table 6.

Since biochemical typically have charge dependent on their pH environment, attaching biochemicals with strong pH sensitivity enable the bioresistor to be used as a pH sensor. FIGS. 14 and 15 are examples of isoelectric curves for common biochemicals commercially available. Many examples exist. A selection for sensitivity targeting a pH range can be made by judicious choice of bioresistor attached biochemicals.

Enhanced binding sites are possible. Techniques such as Silanization, addition of bio attaching films, such as a polymer, and attachment of recognition elements may be assisted by using an appropriate substrate coating film. $Si_3N_4$, by way of example, provides a number of binding sites to which beads, recognition elements, or films are adhered. Such recognition attachment for certain materials is assisted by Silanization and by plasma activation.

Surface functionalization is used for attachment and for pH control. Surface functionalization is well known in the biochemical polymer art. Such functionalization for recognition element binding and for other objectives may be used and is compatible with the current invention. An example of other objectives included mixing the functional surface units/sites to include both base and acid terminations. Choice of the base and acid function mix is used, as is known, to provide a pre-selected pH surface to assist charge recognition and other functions.

There are various process sequences that are used to manufacture the biosensing resistors. The details vary from fabrication to fabrication depending on the environment, applications, integration with electronics, moisture protection and other details. By way of example, a straightforward fabrication sequence is available for polyresistors. It is assumed here that the polysilicon is doped during deposition, a known technique to those of skill in the integrated circuit fabrication arts. An alternative doping means is that of ion implantation of the poly-Si to provide doping of the same type, or different type, from the poly-Si doping, and thermal processing.

Biosensor sensitivity is controlled by the total charge concentration per sq. cm (area concentration). Various means of doping to predetermined area concentrations are available. Ion implantation and predep doping are commonly known.

Heavily doped (high area free conducting carrier concentration) bioresistors typically reduce sensitivity. However, by designing the bioresistors with resistance values fluctuating (with biochemical attachment) to be maximally compatible with ease of ohmmeter measurement using off the shelf ohmmeters. Such measurements should be in a resistance range that undesirable pick up of 60 or 120 Hz from local lines, or other interfering noise such as microphonics, is not a problem. Very high resistances are to be avoided, generally for these reasons. Contemporary ohmmeters (multimeters) can easily measured to 0.1% and more expensive ones to better than $10^{-3}$%. Thus, heavily doped resistors are used to an extent in order to provide dynamic range and other advantages.

Ion implants may be used to ensure that the concentration of mobile charge is at the top surface of the poly-Si. If contact potential is to be measured, the distance from the charge carriers of which the concentration is modified by attaching biochemicals is kept to a minimum. This is accomplished by keeping the top layer of oxide, nitride and any other insulator layers thin since it is the electric field that actually alters the free charge carrier concentration.

Doping of the resistor can also be affected by using the predep technique. The temperature and duration of the predep, together with the saturation solubility curves for the dopant in Si can be used to control the total does, or predep concentration/$cm^2$. Concentrations as low of $10^8/cm^2$ or $1/\mu M^2$ or lower may be achieved in this manner. Low surface concentrations result in higher resistances measured in $\Omega/\square$ (ohms per square). Table 4 provides an approximate measure of resistances in $\Omega/\square$ for low predep doses.

Resistor integration into circuits for selected output sensing parameters is possible. Whereas the bioresistor is the sensing element, it is possible to integrate resistors into circuits to provide a useful sensor output parameter. By way of example, an RC oscillator has an output frequency related to the resistance in the RC component. Such frequency and frequency change arising from biochemical influence on the bioresistor is easily measured with modest cost off-the-shelf frequency counters. A second example is to use the resistance to provide a proportional pulse length, or to use the resistance to provide a time delay. Both parameters may then be measured to determine the biochemical sensing.

A polysilicon resistor basic fabrication outline is presented by way of example. Processes and masks:

1. Grow thin layer of oxide
2. 2000 A-3000 A layer of nitride
3. Deposit thin layer of oxide for surface trap reduction and control
4. Deposit Poly (doped during deposition or by ion implantation). Choose deposition time to result in a thickness desired, e.g., as shown in Table 1-4.

5. Implant Poly if required to achieve pre-selected resistor dopant and resultant free carrier concentration
6. Polysilicon resistor geometry is defined using etching techniques or liftoff techniques. Mask I defines the shape of the resistor with contacts, as shown in FIGS. 10B and 10C. Photoresist may be used and removed later by ashing.
7. Grow thin layer of oxide (>100 A). Deposit additional oxide if desired, to protect resistor region. The thermal oxide is grown to ensure minimum trap states at the poly Si interface.
8. Contact windows opened through the oxide. Mask II open contacts windows as represented by contacts in FIGS. 8B and 10B.
9. Implant ohmic contacts through contact windows in usually manner (heavy doping to provide tunneling ohmic contacts)
10. Remove the protective oxide or photoresist or both
11. Deposit insulator, e.g., oxide or nitride or other materials. A thin grown oxide is grown followed by a protective nitride layer.
12. Open Windows to contact regions. Mask III.
13. Al deposition
14. Pattern Al. Mask IV.
15. Deposit protective nitride and/or other materials to protect Al interconnects
16. Open windows to contact pads and to bioresistor active area insulator top. Mask V.

Other processes will be advantageous under certain conditions, e.g., where the resistors are integrated with integrated circuits for preferred sensor parameter output formats and/or integrated with addressing analog and/or digital circuitry.

The sensors of the present invention may be used for protein sensing, including antibodies, as well as oligos, DNA, c-DNA, RNA of various types, recognition elements, proteins and other biochemicals and chemicals.

The sensor may also be used for virus and bacteria sensor. For virus sensing, the entire virus may be bound to a recognition element and detected. Alternatively, a protein on the virus sheath or RNA component may be detected. Entire bacterium may be bound to a collection of recognition elements, e.g., to a collection of antibodies bound to the sensor surface. The entire bacterium may be sensed or component epitopes or DNA components may be sensed. If entire bacteria are bound to the surface, the system may also be lysed to leave charge epitopes as the sensed target.

Knowledge of the relative amount of charge found on biochemicals is needed to recognize the functionality of the system. It is the area density that is important, and not the bulk density except in combination with the resistor thickness. The surface density of recognition element and target binding and effective surface density of the resistors charge (top down view) must be recognized as being of the right magnitude in the context of the targets to be senses. Recognition of the combination of these two features is critical in recognizing the simple Si transistors may be used for biosensing.

It is not obvious that the fluid environments will have little adverse effect on such integrated circuit technology resistors. It is very well known in the art that integrated circuit devices, not protected, lead to extreme adverse moisture influence on the circuit performance. Such moisture seriously adversely affects active devices. Because for the polyresistors structures there are no high electric field effects a drain contact or collector contact, the premature breakdown seen for FET structures for high sensitivity measurement conditions is not such an issue. For FET biosensor structures, it is critical if moisture influences are present that the substrate is floated; neither grounded nor biased.

The use of very thin oxides allows for rapid response of the oxide moisture uptake to near equilibrium. This approach permits fast response to the fluid environment if needed. Thus, drift is for bioresistors is expected to be not nearly so problematic for the bioresistors described herein as it is in FET devices. This is due in part to the absence of a drain high field region.

To protect against moisture, silicon nitride layers may be used to provide significant or partial protection from moisture. However, adverse surface trapping is to be avoided through judicious fabrication that protects the semiconductor surface area.

Resistor area and value must be judiciously selected as described above. Resistances too high result in adverse outside signal influences and increased instrumentation costs. Resistor area must be selected to provide localization of recognition element application both for discrete sensors and for arrays of sensors using robotic liquid delivering devices.

It is also non obvious that a simple resistor can be used for biosensor and with such high sensitivity and such large dimensions. Indeed, the large dimensions are an issue and desirable since it is very easy to fabricate such devices with contemporary integrated circuit technologies and to integrate them with current integrated circuits such as CMOS circuits. Small dimensional devices such as those with a nanometer dimension or so are problematic for several reasons including poor yields. Of consequence is the difficulty of controlling the placement of recognition elements in arrays and of providing certain recognition element densities using technologies such a bead attachment if one or more dimensions are on the nanometer scale.

Further, such thin or narrow resistors are problematic due to their large resistance and attendant difficulty of measurement, except with expensive instrumentation and complex measurement techniques. Dimensions from fractions of a micron (>0.1 micron) to micron level are easy to manufacture in low cost fabrication environments because of the ease of defining these dimensions. Resistances easily measured can be fabricated in the micron and sub-micron ranges as exemplified in the attached tables. Ideally, such resistors are preferably in the micron range. The ability to put very high density of multiple different recognition elements on a single bioresistor provides a very attractive and useful application for testing for multiple different targets using a single bioresistor device.

For bioresistor arrays, the use of robotic spotters to place different combinations of recognition elements are pre-selected locations in the array requires bioresistor spacing appropriate to the robot placement limitations.

Of consequence is the application of micro or nano drops of liquid containing recognition elements or reactive chemicals, such as drugs, just covering the biosensor is important. Large amounts of bio charge outside of the biosensor area can result in shorting of devices and/or modification of the measured resistance area. The regions surrounding the biosensor may be inverted or accumulated to degradation of the sensor chip or sensor array chip. Thus, careful selection of bioresistor dimension and placement is important in providing ease of measurement (appropriate resistance values) and absence of bleeding of the robotic droplet across multiple sensors.

Nanometer devices may be problematic. Devices with too small a lateral area dimension can result in deleterious effects such as extraneous signal pickup, microphonics, yield problems and recognition element and surface preparation problems.

The cost of packaging is always an issue. Using convenient existing packaging technologies including robotic placement in automated systems reduces costs. Generally speaking, larger dimensional packages are needed to maintain low cost applications. Nanometer devices thus do not take advantage of existing packaging to best effect. One objective to always consider is cost. Special packaging in tiny dimensions may be problematic given that the biosensor must be exposed to the target containing material and manipulated in the measurement environment.

Reduced difficulty in measurement and instrumentation use for applications for practitioners who are not technically proficient in instrumentation complexities is a major consideration. For example, in applications such as homeland security and blood banking, practitioners will come in with other skill sets such as public health management. These and others will not be trained generally in the niceties of complex technologies and instrumentation use. However, most individuals have no difficulty in using a simple ohmmeter testing to measure resistance and resistance change in order to determine if certain diseases are present. The high sensitivity of the bioresistor devices reduces costs of the number of antibodies needed.

Examples of chemical targets and applications regimes follow.

A partial list of biosensor applications target molecules is indicated in Table 5. The list is by way of example. Applications targets are not limited to the list in Table 5.

Applications of the Si based biosensor platform are described in general applications regimes, by way of example, by the list provided in Table 6. Table 6 is intended to be a list of applications by way of example. Applications are not intended to be limited to this partial list.

While the invention has been described with reference to specific embodiments, modifications and variations of the invention may be constructed without departing from the scope of the invention.

The invention claimed is:

1. A method of detecting a target nucleic acid, the method comprising:
    applying the target nucleic acid to a detection system, the detection system including a sensor array and a heater, the sensor array and the heater integrated with a substrate;
    cycling the temperature with the heater to melt nucleotide compounds and facilitate polymerase chain reaction (PCR); and
    detecting a pH change associated with a PCR product using a sensor of the sensor array.

2. The method of claim 1, wherein detecting the PCR product further comprises detecting a change in charge in proximity to a surface of the sensor.

3. The method of claim 1, wherein detecting the PCR product further comprises detecting a chemical potential in proximity to the sensor.

4. The method of claim 1, wherein the sensor includes a source, a drain, and a channel interposed between the source and the drain.

5. The method of claim 4, wherein the sensor further comprises an insulating layer disposed over the channel.

6. The method of claim 5, wherein the sensor further comprises a gate region disposed over the insulating layer.

7. The method of claim 6, wherein the gate region receives the PCR product.

8. The method of claim 1, further comprising controlling the heater with a temperature controller to cycle the temperature of the substrate.

9. The method of claim 8, wherein controlling the heater with the temperature controller includes measuring a temperature with a sensor.

10. The method of claim 1, wherein the detection system further comprises a temperature sensor and a temperature controller for sensing and controlling the substrate temperature.

11. The method of claim 1, wherein the heater is a resistance heater.

12. An apparatus comprising:
    a substrate;
    a sensor array integrated with the substrate, a sensor of the sensor array including a source, a drain, a channel interposed between the source and the drain, an insulating layer disposed over the channel, and target receptors disposed over the insulating layer, the target receptors detecting a pH change associated with a product of a polymerase chain reaction (PCR) responsive to a heater heating the substrate.

13. The apparatus of claim 12, wherein the heater is configured to cycle the temperature of the substrate to melt nucleotide compounds and facilitate polymerase chain reaction (PCR).

14. The apparatus of claim 12, further comprising a temperature sensor integrated with the substrate.

15. The apparatus of claim 12, further comprising a temperature controller to control a temperature using the heater and measured by the temperature sensor.

16. The apparatus of claim 12, wherein the heater is a resistive heater.

17. A method for analyzing a molecular compound, the method comprising:
    applying the molecular compound to a detection system, the detection system including a sensor and a heater, the sensor and the heater integrated with a substrate;
    dissociating the molecular compound; and
    detecting quantitative information related to the molecular compound with the sensor;
    wherein the molecular compound is a nucleotide compound, wherein dissociating the molecular compound includes cycling the temperature with the heater to melt the nucleotide compound and facilitate polymerase chain reaction (PCR), wherein detecting the quantitative information includes detecting a pH change associated with a PCR product using the sensor of the sensor.

18. The method of claim 17, wherein detecting includes detecting a change in charge in proximity to a surface of the sensor.

* * * * *